United States Patent
Gibson

(10) Patent No.: US 9,519,068 B2
(45) Date of Patent: Dec. 13, 2016

(54) X-RAY DETECTION APPARATUS

(71) Applicant: IBEX Innovations Ltd, Sedgefield (GB)

(72) Inventor: Gary Gibson, Sedgefield (GB)

(73) Assignee: IBEX INNOVATIONS LTD., Sedgefield (GB)

(*) Notice: Subject to any disclaimer, the term of this patent is extended or adjusted under 35 U.S.C. 154(b) by 0 days.

(21) Appl. No.: 14/356,920

(22) PCT Filed: Nov. 8, 2012

(86) PCT No.: PCT/GB2012/052772
§ 371 (c)(1),
(2) Date: May 8, 2014

(87) PCT Pub. No.: WO2013/068745
PCT Pub. Date: May 16, 2013

(65) Prior Publication Data
US 2014/0321616 A1     Oct. 30, 2014

(30) Foreign Application Priority Data

Nov. 8, 2011  (GB) .................................. 1119257.2

(51) Int. Cl.
*G01T 1/00* (2006.01)
*G01N 23/00* (2006.01)
(Continued)

(52) U.S. Cl.
CPC ................. *G01T 1/20* (2013.01); *G01N 23/04* (2013.01); *G01T 1/2985* (2013.01)

(58) Field of Classification Search
CPC ......... A61B 6/4291; G01N 23/04; G01T 1/20; G01T 1/2985
See application file for complete search history.

(56) References Cited

U.S. PATENT DOCUMENTS 5,981,959 A    11/1999  Apte
6,201,850 B1    3/2001  Heumann
(Continued)

FOREIGN PATENT DOCUMENTS

CN    1127553 A    7/1996
CN    101937094 A    1/2011
(Continued)

OTHER PUBLICATIONS

International Search Report, Application No. PCT/GB2012/052772, dated Jun. 5, 2013.
(Continued)

*Primary Examiner* — David J Makiya
*Assistant Examiner* — Dani Fox
(74) *Attorney, Agent, or Firm* — MacMillan, Sobanski & Todd, LLC

(57) ABSTRACT

X-ray imaging apparatus, which includes an x-ray detector. The x-ray detector comprises a member configured to convert incident x-ray wavelength photons into emitted visible wavelength photons, a position for a material under test, an x-ray source, and a structure configured to perturb an x-ray energy spectrum, each lying on a common axis. The x-ray source is arranged to direct an x-ray energy spectrum along the common axis to impinge upon the member, the structure configured to perturb the x-ray energy spectrum, and positioned material under test. The structure lies between the x-ray source and the member to one side of the position for material under test intersecting the common axis, and the said structure comprises at least three adjacent regions, each region different to immediately adjacent regions and configured to perturb the x-ray energy spectrum differently.

27 Claims, 20 Drawing Sheets

(51) Int. Cl.
*G01T 1/20* (2006.01)
*G01T 1/29* (2006.01)
*G01N 23/04* (2006.01)

(56) References Cited

U.S. PATENT DOCUMENTS

| | | |
|---|---|---|
| 6,516,044 B1 | 2/2003 | Lyons |
| 2002/0146089 A1 | 10/2002 | Robert-Coutant et al. |
| 2004/0174951 A1 | 9/2004 | Hoffman |
| 2006/0056581 A1 | 3/2006 | Hoffman et al. |
| 2007/0152159 A1 | 7/2007 | Short et al. |
| 2007/0183580 A1 | 8/2007 | Popescu et al. |
| 2010/0135463 A1 | 6/2010 | Kang et al. |
| 2011/0155917 A1 | 6/2011 | Nomura et al. |
| 2011/0243382 A1 | 10/2011 | Morton et al. |
| 2012/0036987 A1 | 2/2012 | Guruprasad et al. |

FOREIGN PATENT DOCUMENTS

| | | |
|---|---|---|
| DE | 102007058447 A1 | 6/2009 |
| DE | 102010040578 A1 | 3/2012 |
| EP | 1063538 A2 | 12/2000 |
| EP | 1120666 A2 | 8/2001 |
| EP | 1607769 A1 | 12/2005 |
| GB | 2409268 A | 6/2005 |
| JP | S6398583 A | 4/1988 |
| JP | H04194695 A | 7/1992 |
| JP | H11218579 A | 8/1999 |
| JP | 2009028110 A | 2/2009 |
| RU | 2003956 C1 | 11/1993 |
| WO | 94/23458 A2 | 10/1994 |
| WO | 9624860 | 8/1996 |
| WO | 9838530 | 9/1998 |
| WO | 03096070 A1 | 11/2003 |
| WO | 2006044692 A2 | 4/2006 |
| WO | 2008142446 A2 | 11/2008 |
| WO | 2009125211 A1 | 10/2009 |
| WO | 2009130492 A1 | 10/2009 |
| WO | 2010047401 A2 | 4/2010 |
| WO | 2010103331 A1 | 9/2010 |
| WO | 2010136790 A1 | 12/2010 |
| WO | 2012048274 A2 | 4/2012 |
| WO | 2012063169 A1 | 5/2012 |

OTHER PUBLICATIONS

Patent Act 1977, Examination Opinion, Application No. GB1220128.1, dated May 15, 2013.
Patents Act 1977: Search Report Under Section 17(5), Application No. GB1220128.1, dated May 14, 2013.
Notification of First Chinese Office Action, Application No. CN201280056214.X dated Nov. 16, 2015.
European Examination Report, Application No. EP12812307.2 dated Oct. 5, 2015.
Patents Act 1977: Further Search Report under Section 17, Application No. GB1220128.1 dated Dec. 10, 2015, Searched Claims 20 and 52.
Patents Act 1977: Further Search Report under Section 17, Application No. GB1220128.1 dated Dec. 10, 2015, Searched Claims 29, 30, 61, and 62.
Patents Act 1977: Further Search Report under Section 17, Application No. GB1220128.1 dated Dec. 15, 2015, Searched Claims 22-28 and 54-60.

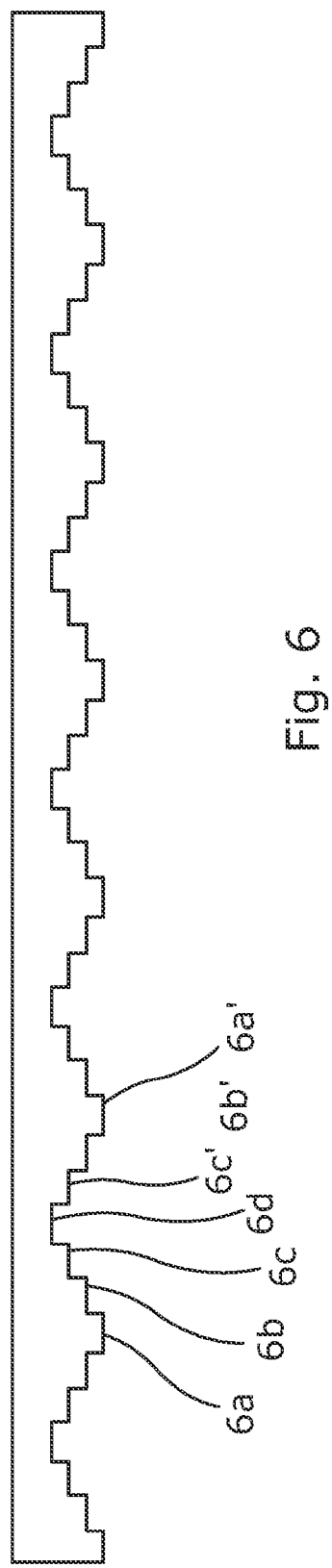

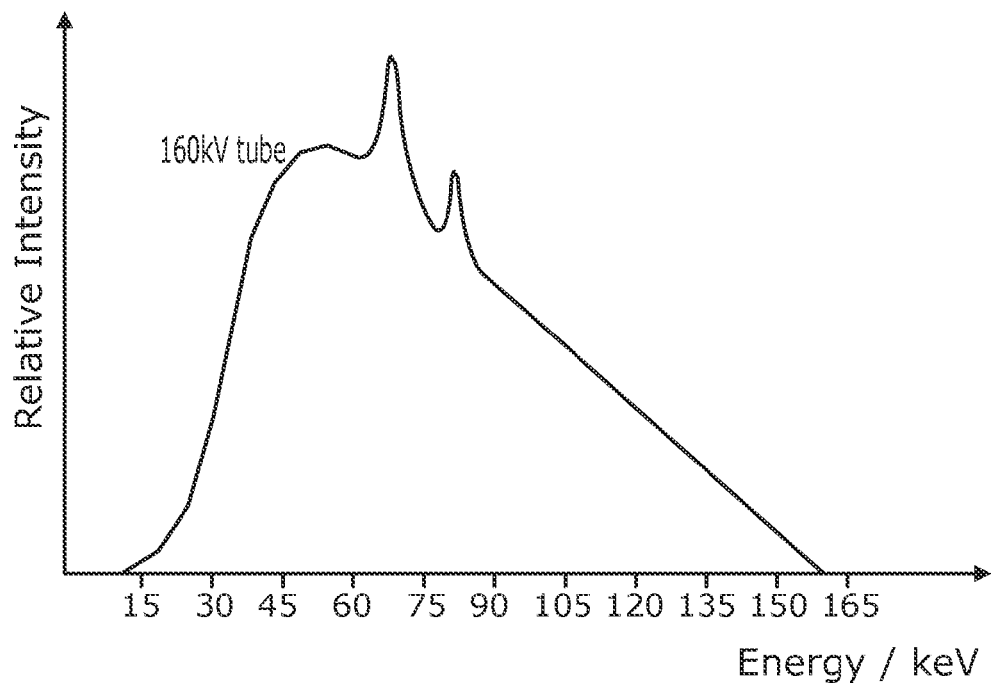
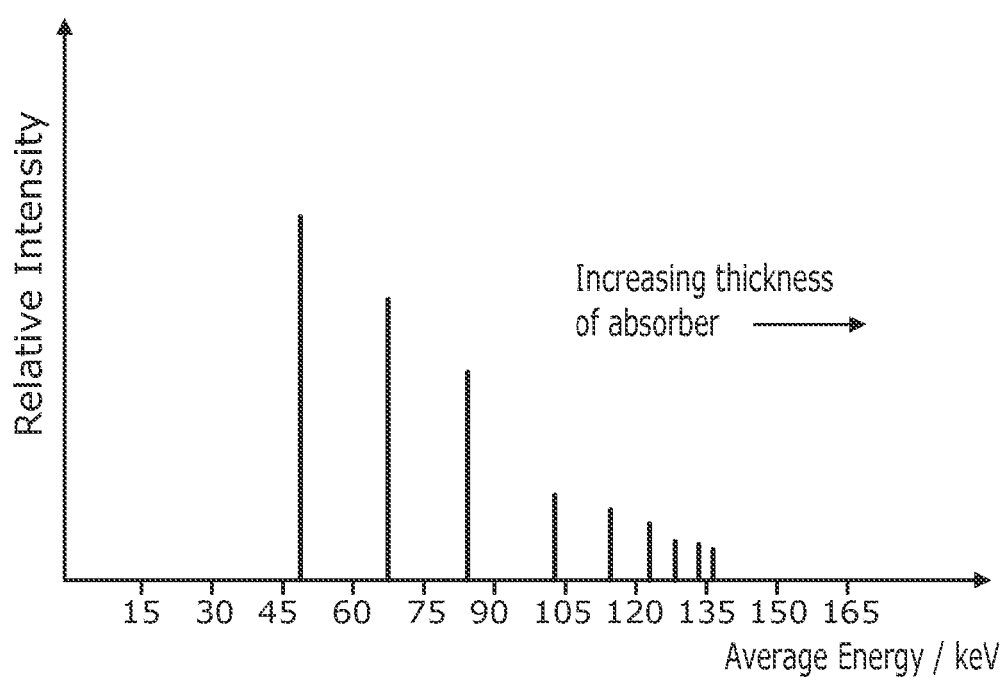
Fig. 12

X-RAY DETECTION APPARATUS

FIELD OF THE INVENTION

The present invention relates to x-ray detectors and in particular to x-ray detectors including a scintillator.

BACKGROUND OF THE INVENTION

An x-ray tube outputs radiation across a wide range of energy bands, the distribution of the energy being defined by the accelerating voltage applied to the tube. When x-rays impact a material, they are absorbed as they pass through. X-rays of different energies are absorbed differently which means that the initial x-ray intensity profile changes. Different materials cause a distinctive change in shape of the x-ray intensity spectra and thus if the spectra can be recorded with sufficient accuracy, it is possible to predict the material that the x-rays have passed through.

While the mass absorption coefficient depends upon both the material type and also the energy of the incident photons, the mass absorption coefficient is independent of material thickness and density. Hence, faced with a resultant spectrum, and knowing the starting spectrum, it is possible to deduce the mass absorption coefficient values and hence the material type the x-rays have passed through.

The detection of x-rays falls into two categories. The first is direct detection, where the energy of an x-ray photon impinging upon a particular material can be directly detected.

Direct detection allows materials to be identified in the manner described above.

For example, X-ray detectors such as $LiNbO_3$ or Ge can directly detect the energy of the incident x-rays and thus are able to output the energy spectrum of the x-ray allowing a determination of the material type.

This technology is described in a number of published patent applications. For example:

The international patent application published under number WO2008/142446 describes energy dispersive x-ray absorption spectroscopy in scanning transmission mode involving the calculation of the intensity ratios between successive frequency bands;

The international patent application published under number WO2009/125211 describes an imaging apparatus and method;

The international patent application published under number WO2009/130492 describes the determination of composition liquids; and The international patent application published under number WO2010/136790 describes a method for the identification of materials in a container.

Whilst the techniques set out in the patent applications mentioned above are effective, the detectors themselves present limitations. The direct x-ray detectors needed are very expensive and the electronics required to operate them is relatively unsophisticated. This leads to errors arising from phenomena such as dark noise, pulse pile-up and energy band fluctuations. In addition, it is difficult to achieve detectors with more than 1024 pixels, which restricts detectors to simple area or pure line-scan detectors. These detectors restrict the scope of the available applications that direct detector technology can be applied to.

The second category of x-ray detection is known as indirect detection, where x-ray photons are first converted into a visible light signal by a scintillator, and then the visible light is detected.

Traditional thinking is that during conversion of x-rays to visible light in a scintillator any energy information that the x-ray photon originally had is destroyed, the visible light output of a scintillator representing only the incident photon density. Hence, the use of indirect conversion has traditionally been limited to pure imaging techniques, whereas direct conversion has been deployed in relation to materials identification.

Dual-energy line scanners are a development of x-ray detectors utilising scintillators. Dual-energy line scanners utilise two sets of detectors, each including a scintillator, the two sets of detectors being spaced apart but axially aligned, with the material under analysis situated between the x-ray source and the first of the two scintillators. The scintillators are specified such that a part of the x-ray spectrum emitted by the source and passing through the material is absorbed by the first scintillator, so that the x-ray energy spectrum impinging on the second scintillator is not identical to that impinging on the first scintillator, even when a material for analysis is not present. Hence, the photon emission by each scintillator is different. A material under analysis affects the difference in photon emission by each scintillator. Materials may be identified by looking at the ratio between the photon emission by the respective first and second scintillators.

Another type of dual energy detector is described in EP1063538. Instead of the x-rays passing through the specimen and two axially aligned detectors, a linear array scintillator system is provided comprising alternating scintillator thicknesses, one of the thicknesses of scintillator material providing a signal corresponding to the passage of x-rays through a material of relatively low molecular weight and the other thickness of scintillator material providing a signal corresponding to the passage of x-rays through a material of a relatively high molecular weight. The linear array described is for use with a thin collimated curtain of x-rays that pass through an object under test and impinge upon the linear array scintillator. According to EP1063538, the linear array scintillator can produce a stereoscopic image and discriminate between materials of high and low molecular weight more easily than dual energy detectors of the prior art.

Dual-energy line scanners are effective in identifying materials having a high or a low molecular weights. However, they are not particularly effective in identifying materials having a molecular weight falling between these extremes or in distinguishing the difference in materials with a very similar molecular weight.

The ability to detect a wide range of materials using indirect detection utilising a scintillator would be particularly advantageous. This is because, in comparison to the equipment used for the direct detection of x-rays, equipment for indirect detection utilising a scintillator is comparatively cheap, and also sophisticated electronics have been developed. Further, the resolution available with direct detectors limits the number of pixels into which an image may be divided, at present to about 1000, whereas those using such detectors would like to increase the number of pixels into which an image is divided significantly.

Whilst dual-energy detectors have some material identification capability, that capability is limited.

It would therefore be desirable to provide an indirect x-ray detector including a scintillator, capable of identifying materials.

SUMMARY OF THE INVENTION

According to a first aspect of the invention there is provided x-ray imaging apparatus, the apparatus including an x-ray detector comprising a member configured to convert incident x-ray wavelength photons into emitted visible wavelength photons, a position for a substance under test, an x-ray source, and a structure configured to perturb an x-ray energy spectrum, each lying on a common axis, wherein the x-ray source is arranged to direct an x-ray energy spectrum along the common axis to impinge upon the member, the structure configured to perturb the x-ray energy spectrum, and positioned substance under test, wherein said structure lies between the x-ray source and the member to one side of the position for substance under test intersecting the common axis, wherein the said structure comprises at least three adjacent regions, each region different to immediately adjacent regions and configured to perturb the x-ray energy spectrum differently.

Advantageously, the regions lie laterally of one another, and preferably the structure comprises a plurality of regions lying laterally of one another, and preferably in two orthogonal directions.

Preferably, the member configured to convert incident x-ray wavelength photons into emitted visible wavelength photons is a scintillator.

The scintillator may include a scintillator layer and a backing layer.

Advantageously, the plurality of regions are formed in an array, and the array may repeat itself in the structure. For example, the plurality of regions may comprise a three by three array of nine regions, and the structure may include a multiplicity of such arrays.

Preferably, the structure is planar or non-planar. The structure may be curved in at least one plane.

Preferably, the difference between adjacent regions is the thickness of the material of the structure in adjacent regions.

The structure may include a plurality of protrusions or depressions, the thickness of said protrusions or depressions changing in at least one direction thereof, each protrusion or depression providing at least three adjacent regions configured to perturb the x-ray energy spectrum.

Preferably, the protrusions or depressions are pyramidal in shape.

The structure may comprise a non-metallic layer having a multiplicity of depressions formed therein, each depression filled with metal. Preferably, the structure comprises a first non-metallic layer having a multiplicity of depressions formed therein and a second metallic layer including a corresponding number of protrusions each protrusion mating with filling a corresponding depression.

The second layer may cover the surface of the first layer in which the openings to the depressions are situated.

Adjacent depressions or protrusions may be separated from one another by x-ray perturbing material and wherein the material separating adjacent depressions or protrusions may constitute one of the at least three regions.

The non-metallic layer may be formed of silicon.

The difference between adjacent regions may be the material from which the individual adjacent regions of the structure are formed.

The adjacent regions may differ in thickness and in the material from which they are made. For example, the structure may comprise a substrate of even thickness, and the individual regions may be formed on a surface thereof by building up discrete layers of material on adjacent regions. The number of layers and/or the materials of those layers may differ. Techniques such as PVD, electro-deposition or laser ablation may be used to form the individual regions.

In addition, the regional variation may be created by stacking layers of foils with cut-out regions one on top of each other so that the cut out regions stack in such a way to create a variety of thicknesses in a lateral sense.

Another alternative would be to stack a series of wire meshes together in a similar fashion to the foils such that a variation in material thicknesses are formed. This is similar to techniques used to form neutral density filters.

Another alternative is to start with a certain thickness of material and cut out regions to create differing thicknesses. This could be done by laser micro-machining or ion-beam milling amongst the many techniques.

Where the material property of the structure, such as thickness of the structure changes continuously rather than by steps, taking any point on the structure, if its property (thickness) is different to the thickness of the structure at an adjacent point, then those two points may each be considered to be regions configured to perturb the x-ray energy spectrum differently.

The said structure configured to perturb the x-ray energy spectrum may be comprised in the scintillator, and may be in either the scintillator layer or a backing layer thereof.

According to a second aspect of the invention there is provided x-ray detector suitable for use in an x-ray detection apparatus according to the first aspect of the invention and comprising a member configured to convert incident x-ray wavelength photons into emitted visible wavelength photons and a structure for alignment with an x-ray energy spectrum source, the structure configured to perturb the x-ray energy spectrum, and the structure comprising at least three adjacent regions, wherein each region is different to immediately adjacent regions, each adjacent region configured to perturb the x-ray energy spectrum differently.

Advantageously, the regions lie laterally of one another, and preferably the structure comprises a plurality of regions lying laterally of one another, and preferably in two orthogonal directions.

According to a third aspect of the invention there is provided a structure configured to perturb an x-ray energy spectrum incident thereon, the structure comprising at least three adjacent regions, wherein each region is different to immediately adjacent regions, each adjacent region configured to perturb the x-ray energy spectrum differently.

Advantageously, the regions lie laterally of one another, and preferably the structure comprises a plurality of regions lying laterally of one another, and preferably in two orthogonal directions.

Advantageously, the plurality of regions are formed in an array, and the array may repeat itself in the structure. For example, the plurality of regions may comprise a three by three array of nine regions, and the structure may include a multiplicity of such arrays.

Preferably, the structure is planar or non-planar. The structure may be curved in at least one plane.

Preferably, the material difference between adjacent regions is the thickness of the material of the structure in adjacent regions.

The structure may include a plurality of protrusions or depressions, the thickness of said protrusions or depressions changing in at least one direction thereof, each protrusion or depression providing at least three adjacent regions configured to perturb the x-ray energy spectrum.

The protrusions or depressions may be pyramidal in shape.

The structure may comprise a non-metallic layer having a multiplicity of depressions formed therein, each depression filled with metal.

Advantageously, the structure comprises a first non-metallic layer having a multiplicity of depressions formed therein and a second metallic layer including a corresponding number of protrusions each protrusion mating with filling a corresponding depression.

Preferably, the second layer covers the surface of the first layer in which the openings to the depressions are situated.

Adjacent depressions or protrusions may be separated from one another by x-ray perturbing material and wherein the material separating adjacent depressions or protrusions constitute one of the at least three regions.

Preferably, the non-metallic layer is formed of silicon.

The depressions in the non-metallic layer are preferably formed by etching. The walls of pyramidal depressions preferably lie at 54.7 degrees to the surface of the non-metallic layer.

The material difference between adjacent regions may be the material from which the individual adjacent regions of the structure are formed.

The adjacent regions may differ in thickness and in the material from which they are made. For example, the structure may comprise a substrate of even thickness, and the individual regions may be formed on a surface thereof by building up discrete layers of material on adjacent regions. The number of layers and/or the materials of those layers may differ. Techniques such as PVD, electro-deposition, laser ablation or 3d-printing may be used to form the individual regions.

In addition, the regional variation may be created by stacking layers of foils with cut-out regions one on top of each other so that the cut out regions stack in such a way to create a variety of thicknesses in a lateral sense.

Another alternative would be to stack a series of wire meshes together in a similar fashion to the foils such that a variation in material thicknesses are formed. This is similar to techniques used to form neutral density filters.

Another alternative is to start with a certain thickness of material and cut out regions to create differing thicknesses. This could be done by laser micro-machining or ion-beam milling amongst the many techniques.

According to a fourth aspect of the invention there is provided method of determining a material property of a substance comprising the steps of:
 a) positioning the substance in an x-ray detection apparatus according to the first aspect of the invention;
 b) causing the x-ray source to direct an x-ray energy spectrum along the common axis;
 c) analysing visible wavelength photons emitted by the member configured to convert incident x-ray wavelength photons into visible wavelength photons.

The detector of the invention is particularly suited to scintillator materials having a strong energy dependence. In the prior art such materials are avoided where possible because of the difficulties in separating out energy and thickness information relating to the material through which the x-ray has passed. In the prior art, wherever possible scintillator materials giving an output of one visible light photon for one incident x-ray photon have been selected.

The detector of the invention, which is an indirect detector, provides for materials identification of objects combined with high resolution imaging. This represents a significant advantage over direct detectors where the size of two-dimensional cameras is very much more limited.

The imaging apparatus of the invention is particularly suited to the high resolution imaging of complex shapes with a limited number of material systems. For example, the inspection of printed circuit boards and general electronics, and the detection and identification of radio-isotopes in a cluttered or shielded environment.

There are numerous other areas where imaging apparatus may usefully be deployed, for example in non-destructive testing, medical devices, the food industry, etc.

The substance may be a solid, a fluid or a combination of the two, for example human/animal tissue, or food substances.

BRIEF DESCRIPTION OF THE DRAWINGS

In the Drawings, which illustrate preferred embodiments of an x-ray detector according to the invention, and components thereof:

FIG. 6 is a cross-sectional view on the axis A-A of FIG. 5 of an interference plate of the detector illustrated in FIG. 5;

FIG. 12 is a graph illustrating the detected intensity v energy spectrum in a detector according to the invention, the x-ray source being that of FIG. 9, the x-rays having passed through the same material under analysis;

FIG. 13b is a plan view of component parts of an interference plate of the type illustrated in FIG. 13a;

FIG. 16b illustrates exploded side and schematic views of the embodiment illustrated in FIG. 16a.

DETAILED DESCRIPTION OF THE PREFERRED EMBODIMENTS

Figure 1:
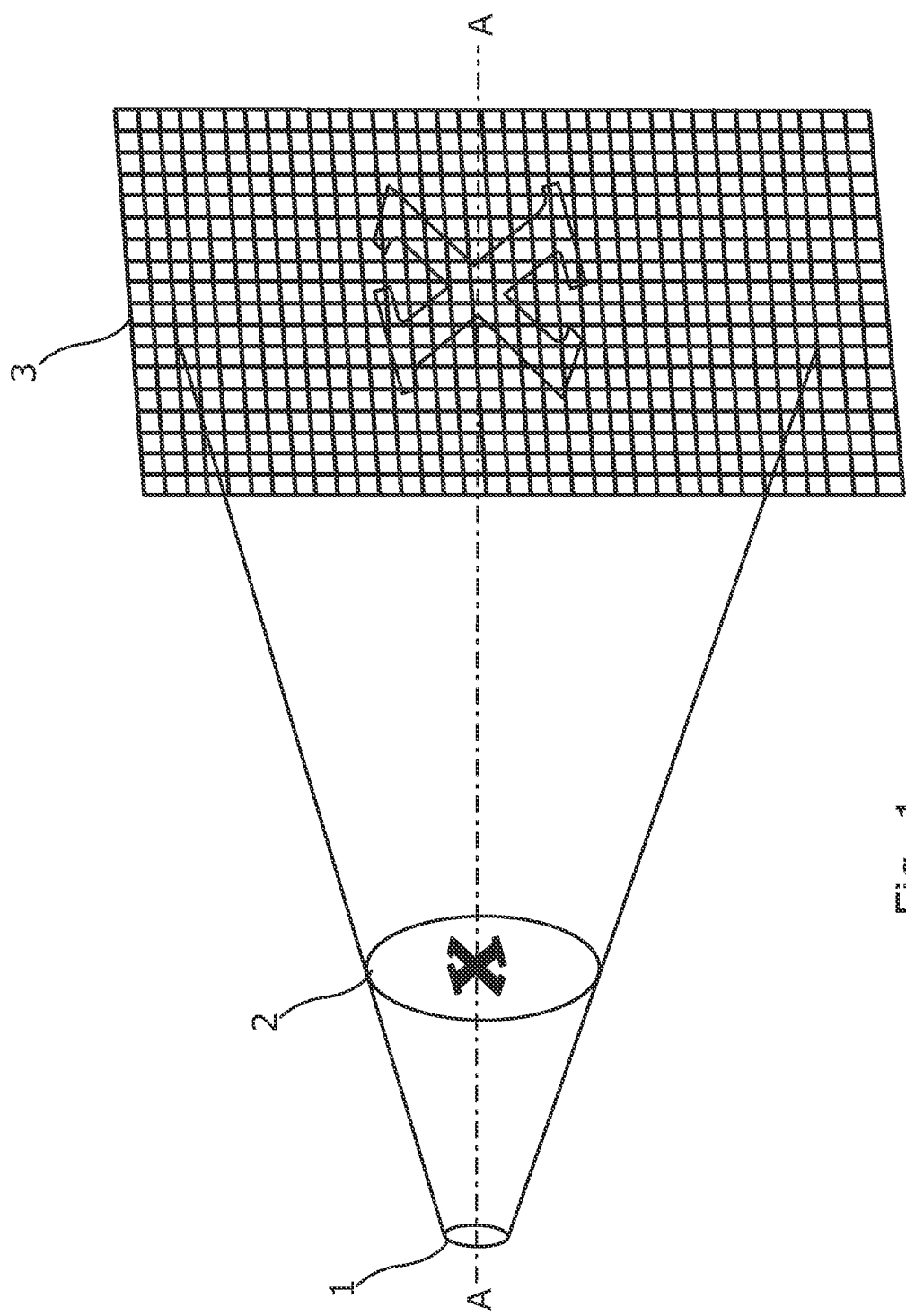
FIG. 1 is a simplified schematic representation of an x-ray detector according to a first embodiment of the invention.

Referring now to FIG. 1, for the sake of clarity, the detector is shown in its most basic form and comprises an x-ray source 1, an object 2 and a pixelated scintillator plate 3. X-rays emitted from the x-ray source 1 pass through the object 2, the attenuated x-rays that have passed through the object 2 being detected by the scintillator plate 3. The x-ray source 1, object 2, and scintillator plate 3 lie on a common axis A-A.

Figure 2:
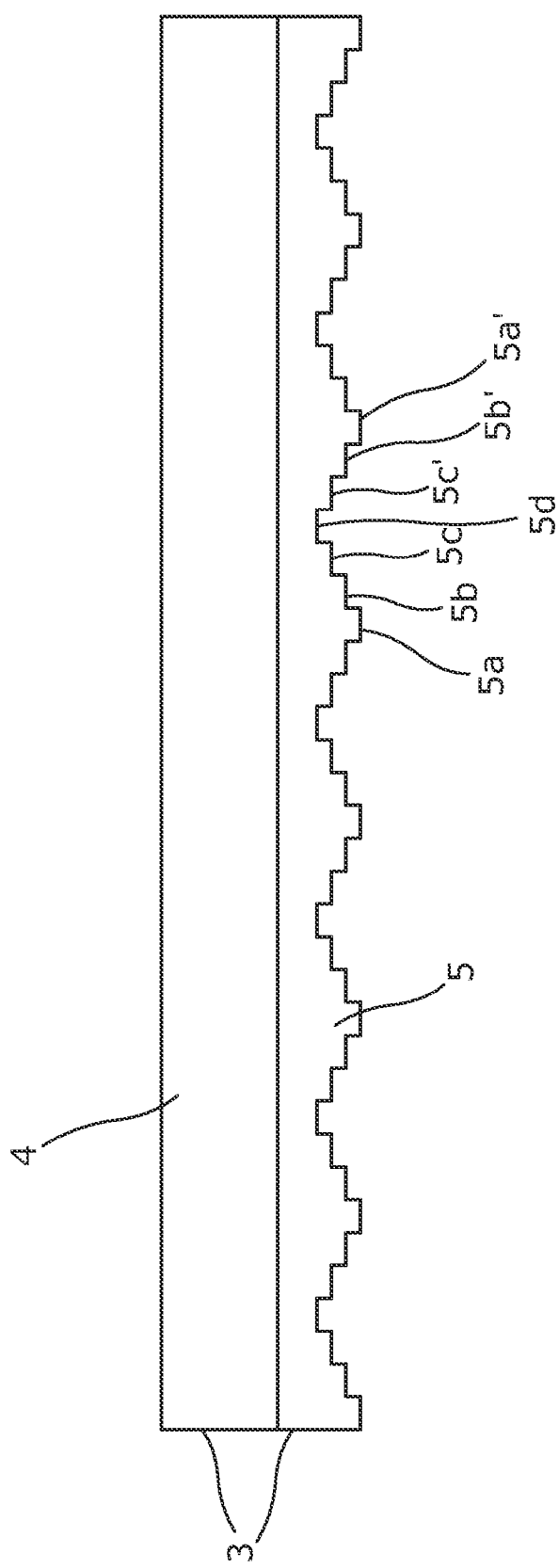
FIG. 2 is a cross-sectional view of a first embodiment of a scintillator plate of the detector illustrated in FIG. 1.

FIG. 2 illustrates in cross-section a first embodiment of a scintillator plate 3 which comprises a scintillator layer 4 and a backing layer 5. The scintillator layer 4 is of a uniform material and has a uniform thickness. Preferably, the material from which the scintillator layer 4 is formed has a strong response to incident x-ray photon energy. However, the backing layer 5, comprises a multiplicity of regions of differing thickness represented by numerals 5a to 5d. For the sake of clarity only a sample of regions are numbered.

Figure 3:
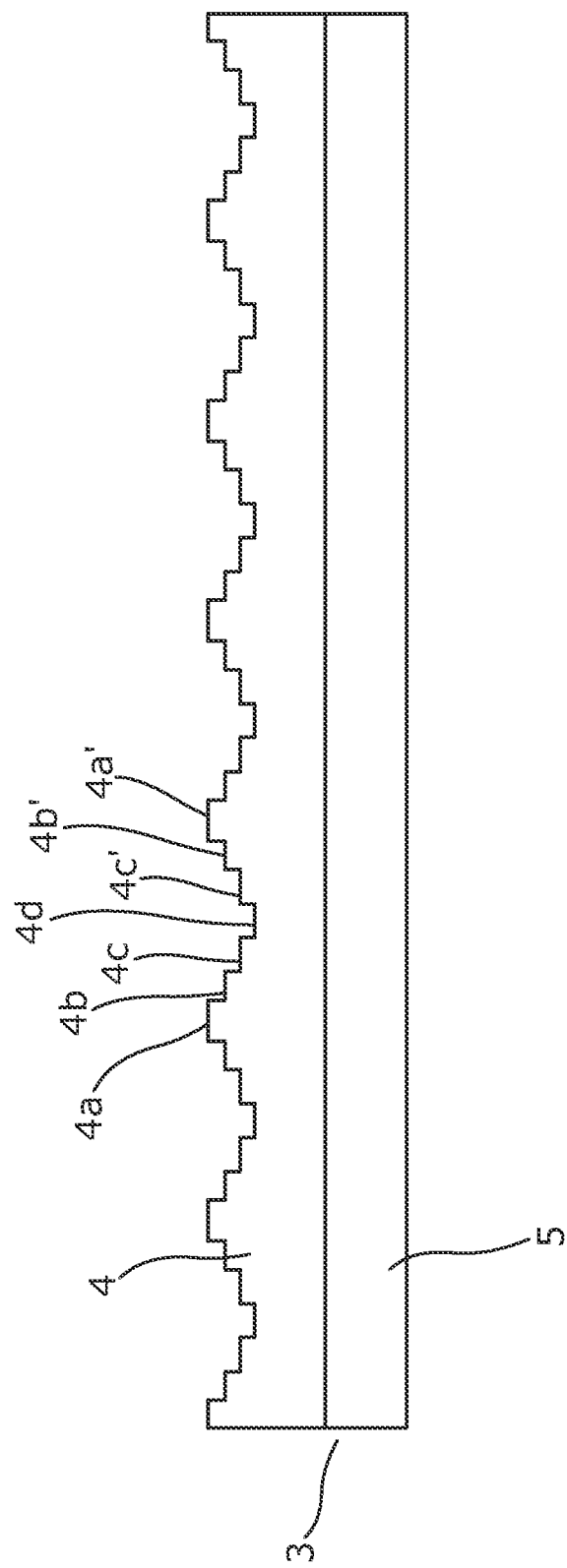
FIG. 3 is a cross-sectional view of a second embodiment of a scintillator plate of the detector illustrated in FIG. 1.

FIG. 3 illustrates in cross-section a second embodiment of a scintillator plate 3 which again comprises a scintillator layer 4 and a backing layer 5. However, in this embodiment the metal (aluminium) backing layer is of a uniform material and a uniform thickness, whereas the scintillator layer 4 comprises a multiplicity of regions of differing thicknesses represented by the numerals 4a to 4d. For the sake of clarity only a sample of regions are numbered. Preferably, the material from which the scintillator layer 4 is formed has a strong response to incident x-ray photon energy.

Figure 4:
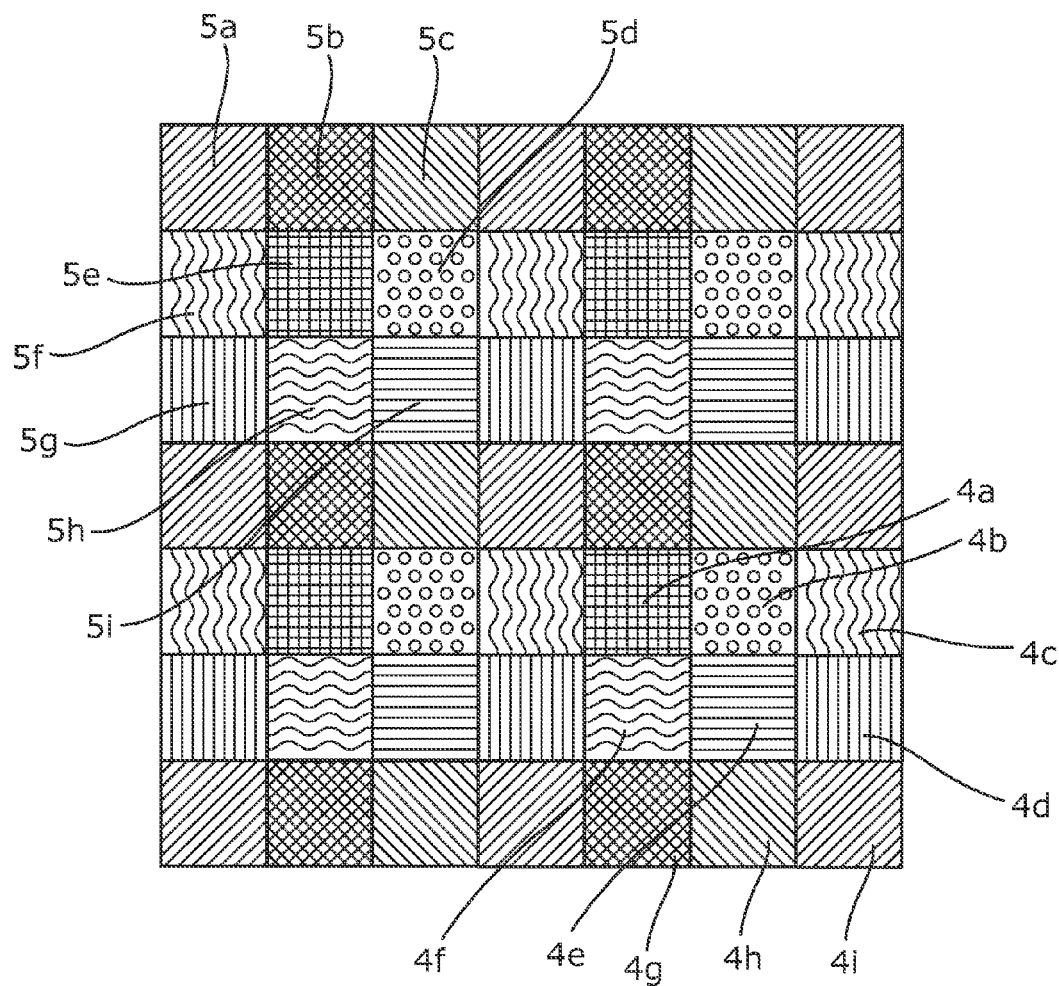
FIG. 4 is a rear view of a scintillator plate illustrated in FIG. 2 and a front view of the scintillator plate illustrated in FIG. 3.

FIG. 4 is a rear view of the scintillator plate illustrated in FIG. 2 and a front view of the scintillator plate illustrated in FIG. 3. The plate 3 provides forty nine regions, based around a repeating array of nine different pixel thicknesses, formed in a three by three block of regions. This arrangement provides that for any three by three group of nine regions the central pixel of the group is surrounded by eight regions each of which has a different thickness and that regions adjacent any one selected pixel are of a different thickness. The bottom right corner of the scintillator plate is numbered as a front view of FIG. 3, and the top left corner is numbered as a rear view of FIG. 2.

The difference in thickness between adjacent regions is approximately 200 micron in the illustrated examples described above.

Whilst the plate 3 provides forty nine regions based around a repeating array of nine different pixel thicknesses, the invention is not limited to this format. For example, the layout of the plate 3 may be based around a repeating array of four different pixel thicknesses in two by two array.

The prior art suggests that in an indirect x-ray detector the scintillator material should provide a flat response to incident x-ray energy. Such a scintillator material may be useful in either of the embodiments illustrated in FIGS. 2 and 3. However, it is preferred that the scintillator material should have a strong energy response, i.e. the number of visible photons produced will relate to both incident x-ray intensity and incident x-ray energy, possible more strongly to incident x-ray energy than to incident x-ray intensity.

Figure 5A:
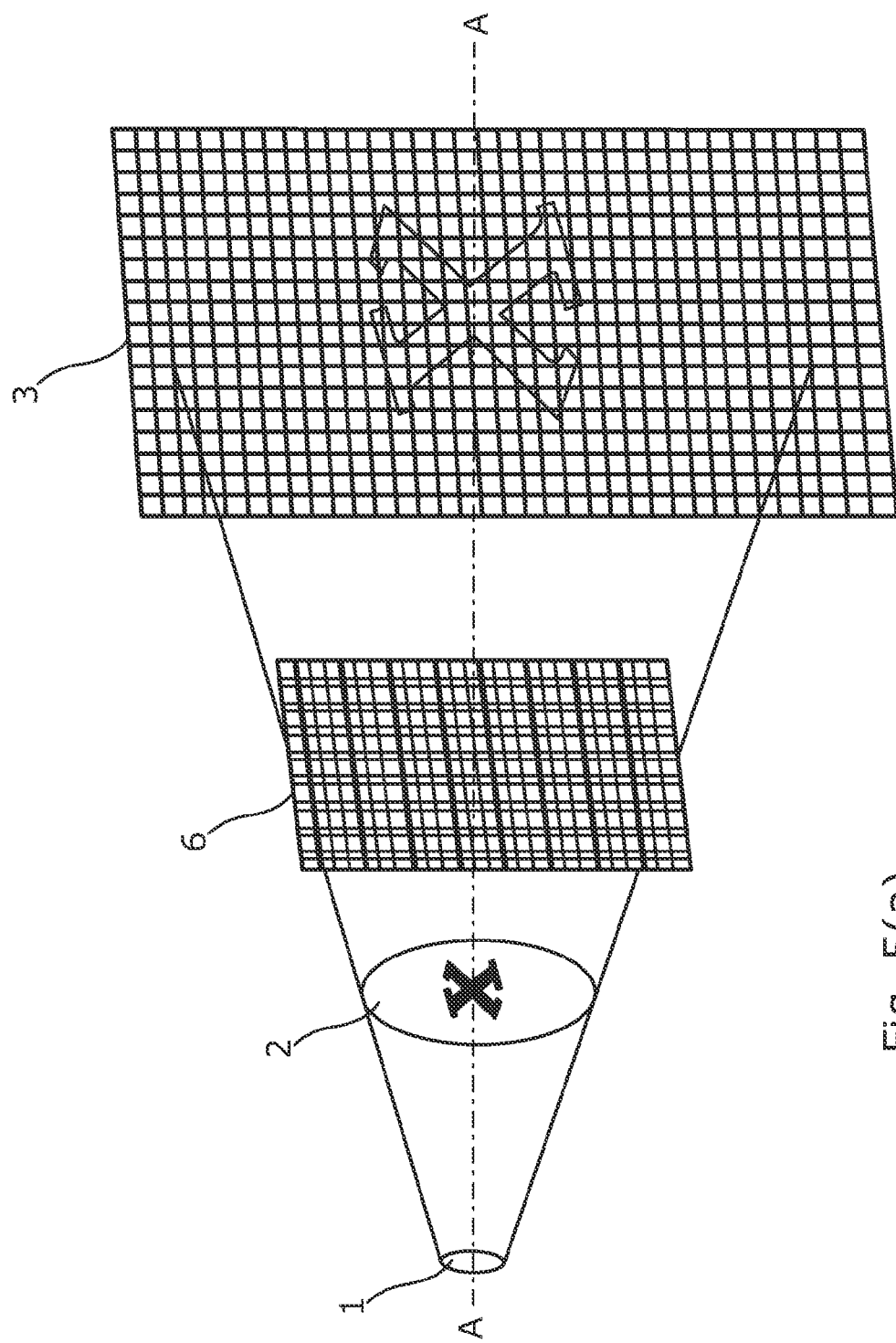
FIG. 5a is simplified schematic representation of an x-ray detector according to another aspect of the invention with a component of the detector situated between the object and the detector.
Figure 5B:
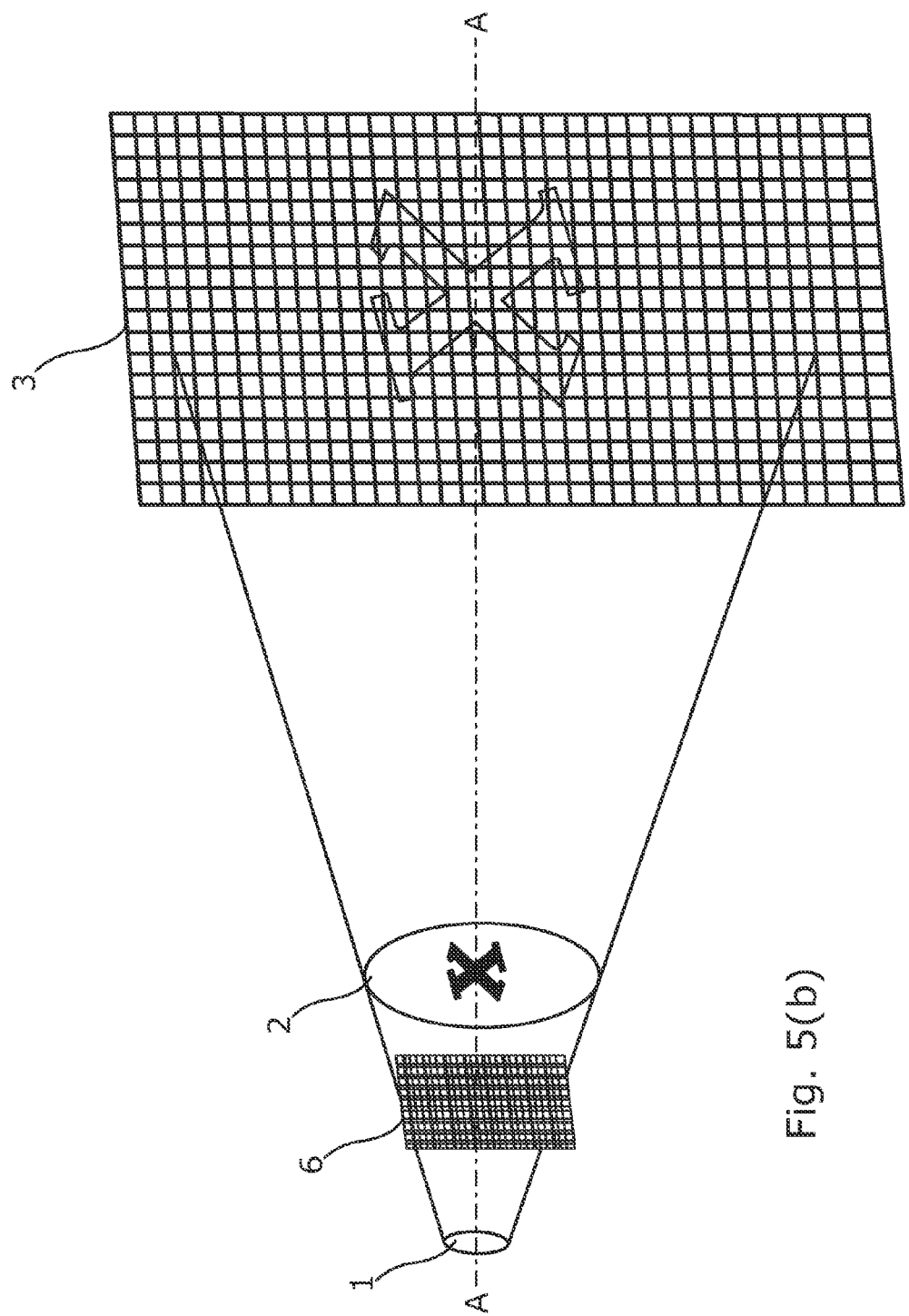
FIG. 5b is simplified schematic representation of an x-ray detector according to another aspect of the invention with a component of the detector situated between the x-ray source and the object.
Figure 7:
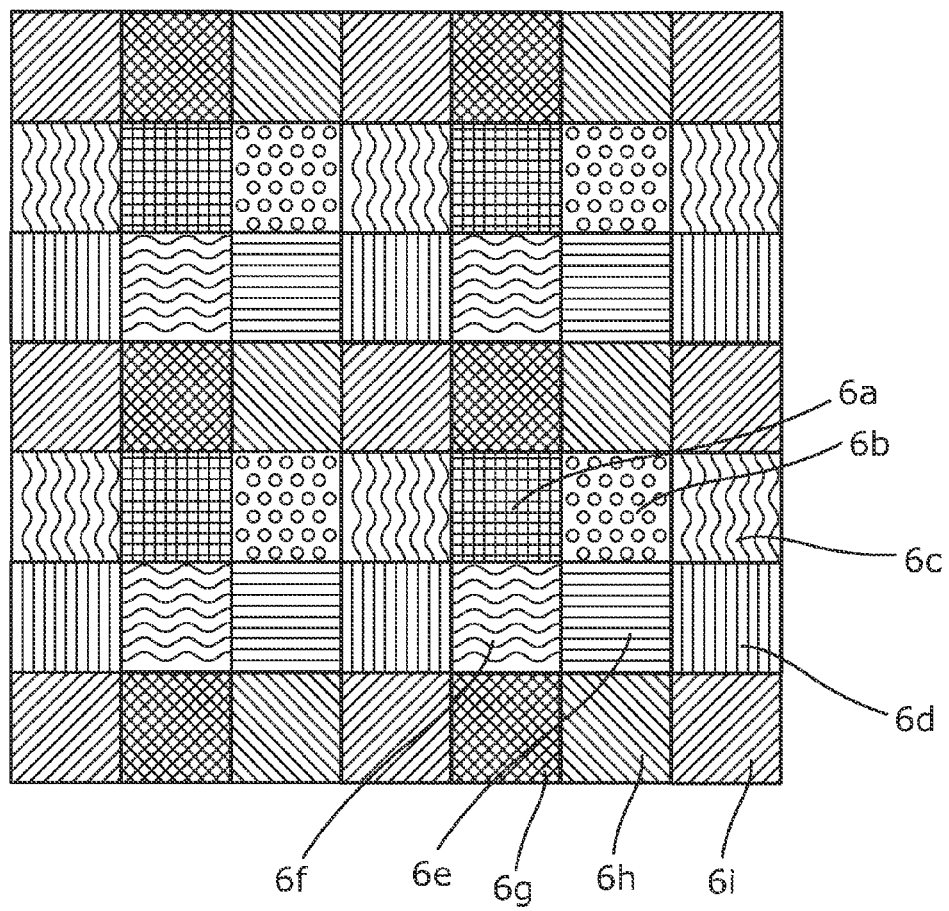
FIG. 7 is a front view of the multi-regioned structure, i.e. an interference plate illustrated in FIG. 6.

FIGS. 5 to 7 illustrate an alternative embodiment of the invention where instead of either the backing plate of the scintillator plate of the scintillator presenting regions of differing thickness, a scintillator of standard construction is used, with an interference plate 6 (which may also be considered to be a multi-absorption plate, i.e. different regions of the plate have different x-ray absorption capabilities), of tungsten for example, being placed between the object and the scintillator as in FIG. 5a, or between the x-ray source and the object as in FIG. 5b. Such a construction may be simpler and less costly to manufacture than a scintillator of the type illustrated in FIGS. 1 to 4. Further, in addition to manufacturing the interference plate such that regions thereof have different thicknesses, it possible that the interference plate may have uniform thickness, with the material difference between adjacent regions being provided by forming the individual regions of the interference plate of different materials.

The interference plate may comprise a substrate with the individual regions formed on or in the substrate. The individual regions may be formed in the base layer by etching or even machining the substrate.

The interference plate may be formed by 3d-printing.

The individual regions shown in FIGS. 2-4, 6 and 7 may represent regions of different thickness.

The individual regions may be formed on the substrate by deposition, for example by a technique well known in the art as "lift-off". An advantage of such a technique is that the material deposited in the "lift-off" process may be the same as the material from which the substrate is formed. The material difference between adjacent regions is the thickness of each pixel. Further, the deposited material may be different to the substrate material, providing for the material difference between adjacent regions to be lie in material type and/or the material thickness.

Figure 8:
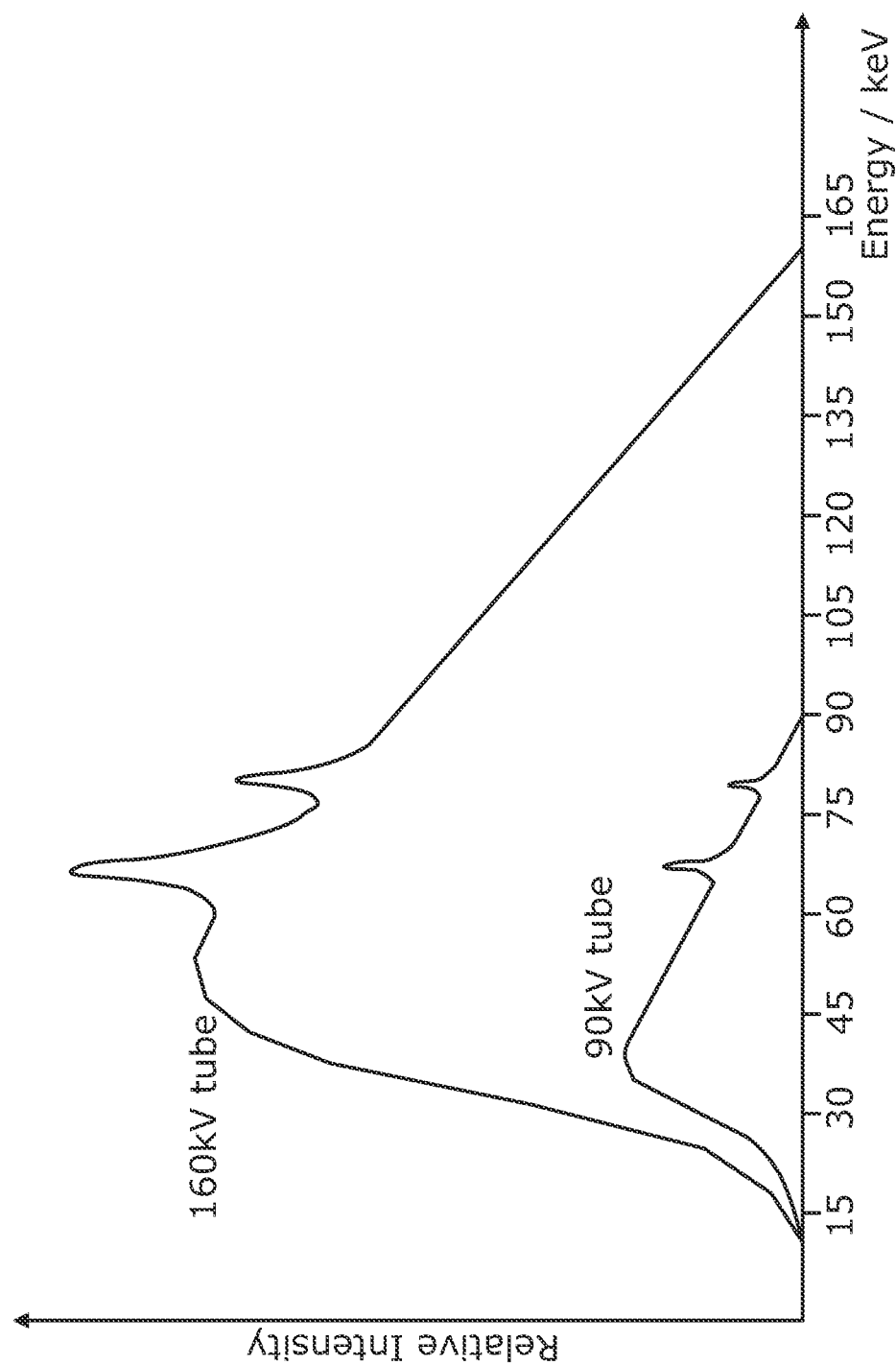
FIG. 8 is a graph illustrating a typical spectrum output intensity v energy for an x-ray source.
Figure 9:
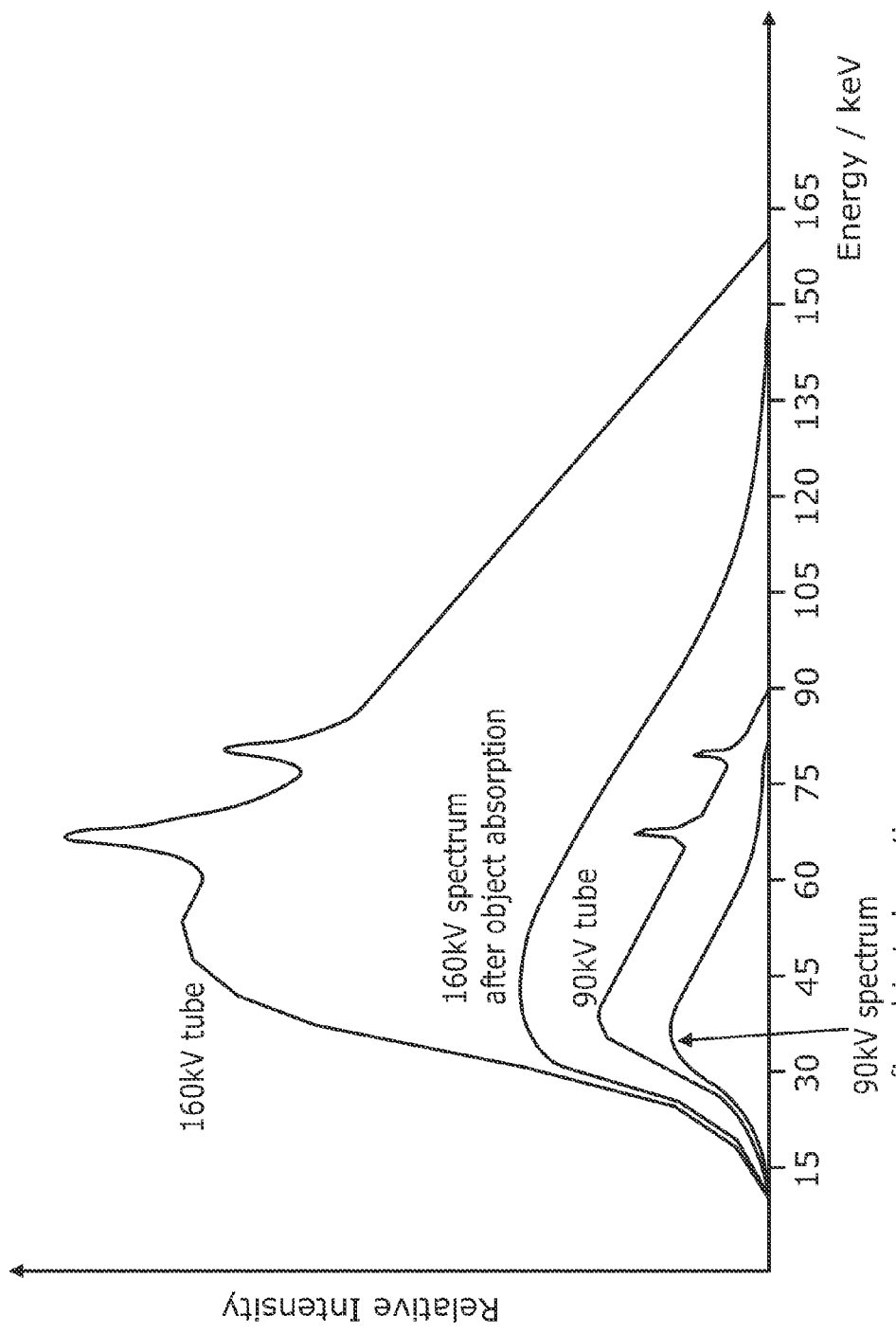
FIG. 9 is a graph illustrating a detected intensity v energy spectrum in a direct detector, the x-ray source being that of FIG. 8, the x-rays having passed through a material under analysis having a uniform thickness.

Referring now to FIG. 8, there is shown a typical intensity versus energy spectrum for x-rays emitted from an x-ray source. When the same x-rays pass through a material of uniform thickness, some of the x-ray photons are absorbed by the material and hence the intensity of the spectrum is reduced, as can be seen in FIG. 9.

Where a direct detector of the type described in the section entitled, "Background of the Invention" is used to detect the x-ray spectrum passing through the material the graph shown in FIG. 9 is what is detected. However, where an indirect detector is used, the output of the detector, i.e. the number of photons in the visible spectrum emitted by the scintillator is largely independent of the energy of incident x-ray photons, and depends only on the intensity of incident x-ray photons. Hence, the intensity versus energy graph for an indirect detector comprises a single line representing an arbitrary mean energy value.

Figure 10:
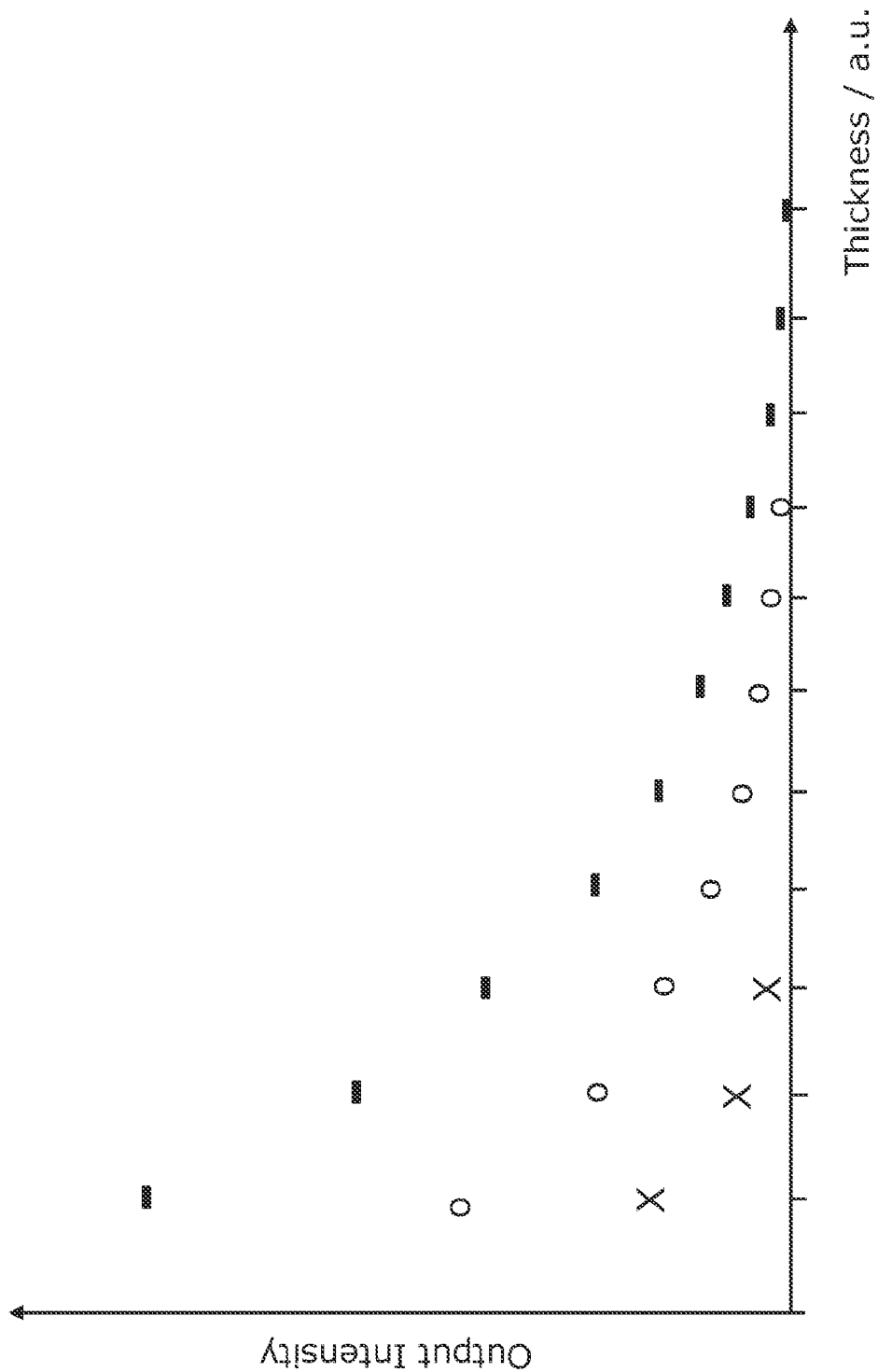
FIG. 10 is a graph illustrating the effect of interference plate thickness on x-ray intensity.

FIG. 10, is a graph showing the variation in output intensity for a particular material depending on the thickness of the material. The three different curves represent incident x-ray photons having low, medium and high energy. The x-ray spectrum emitted from the source as illustrated in FIG. 8 is comprised of x-ray photons having different energies. It can be appreciated from FIG. 10 that the effect of increasing the thickness of the material through which the x-ray photons pass is that those x-ray photons having low energies are absorbed, whereas those with medium and high energies pass through, the x-ray photons with the highest energy passing through the thickest materials.

Figure 11:
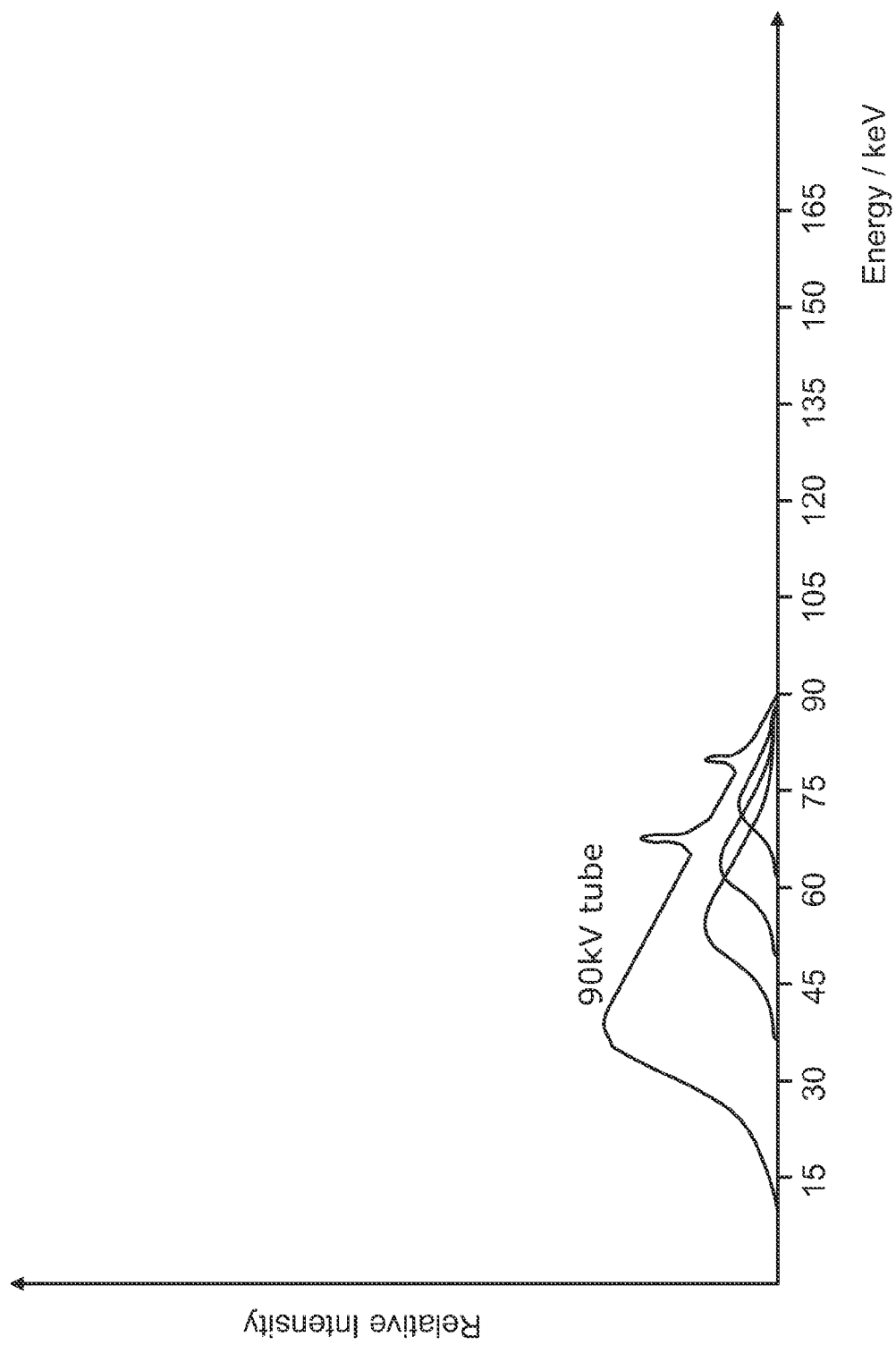
FIG. 11 is a graph illustrating resultant spectra of intensity v energy for an x-ray energy spectrum passing through an interference plate of the invention.

FIG. 11 is a graph of intensity versus energy and shows the individual spectra relating to the low energy x-ray photons passing through the same material, but of different thickness. The right most curve represents the spectra related to the photon having passed through the thickest material.

Hence, it will be appreciated that by passing an x-ray spectrum emitted from a source through a structure comprised of regions of different thickness, a plurality of x-ray spectra will be created, each spectra corresponding to the thickness of material through which the x-ray spectra has passed. When this plurality of x-ray spectra are incident on a scintillator, whilst the energy of the incident spectra may be disassociated with the intensity of the x-ray photons of the spectra, each incident spectra gives rise to an intensity response. Hence, where a three by three array of pixel thicknesses is used, nine different intensity values are generated by the scintillator. FIG. 12 is a graph illustrating such a scintillator output.

The output illustrated in FIG. 9 is for a scintillator having a substantially flat response to energy. The general trend in imaging has been to eliminate scintillator energy response as they result in shadows in the image, which is generally regarded as undesirable. However, in the present invention, the use of a scintillator material whose response to energy is not flat is preferred. Where such a scintillator material is used, greater incident energy results in greater scintillator output intensity. The detector of the invention can utilise such differences in output intensity.

If one refers to the graph shown in FIG. 10, where a scintillator material is used whose output intensity is varies according to the energy of the impinging x-ray photons, it can be appreciated that the difference in output intensity from the scintillator for adjacent regions will be greater than where a scintillator material having a flat response to energy is used. These differences can be utilised to assist in material identification.

X-ray detectors of this type function by comparing the scintillator output for a known material, known combination of materials, or known material or combination of materials and other material properties, such as thickness with what is detected by the detector. Hence, the more possibility for discrimination between materials, material combinations and so forth, the more useful is the detector.

Suitable scintillator materials include CsI(Tl) and NaI(Tl), which are commonly used scintillator materials for mif to high range x-ray photons. They have a high stopping efficiency, and are efficient producers of visible photons. Large area single crystals can be produced easily from these materials, making them ideal for large surface area detectors.

Bi12FeO20(BGO) is another suitable scintillator material. It is especially useful for hard x-rays and soft gamma rays. However, it is more difficult to fabricate in large areas than the alkali halides mentioned above.

Plastic scintillators are also common and have an excellent decay constant, in the order of nanoseconds, compared to microseconds for the inorganic scintillators mentioned above. Also, plastic scintillators are easily formed into complex shapes, typically by moulding, making them ideal for the fabrication of some embodiments of the invention described herein. Polyethalene napthalate has shown excellent scintillation properties and is reasonably durable.

Figure 13A:
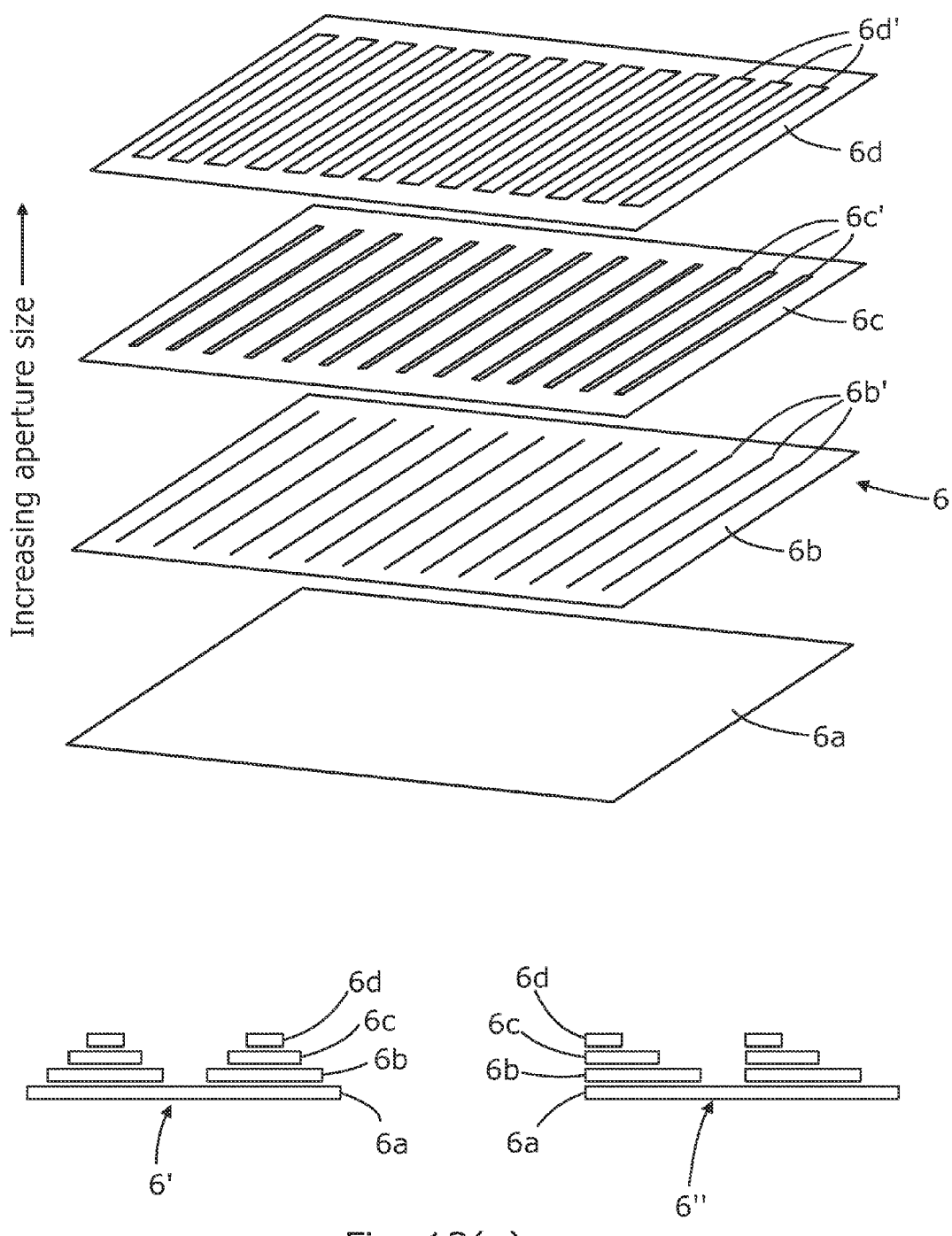
FIG. 13a is an exploded view of an interference plate built up from a number of layers of material.
Figure 13B:
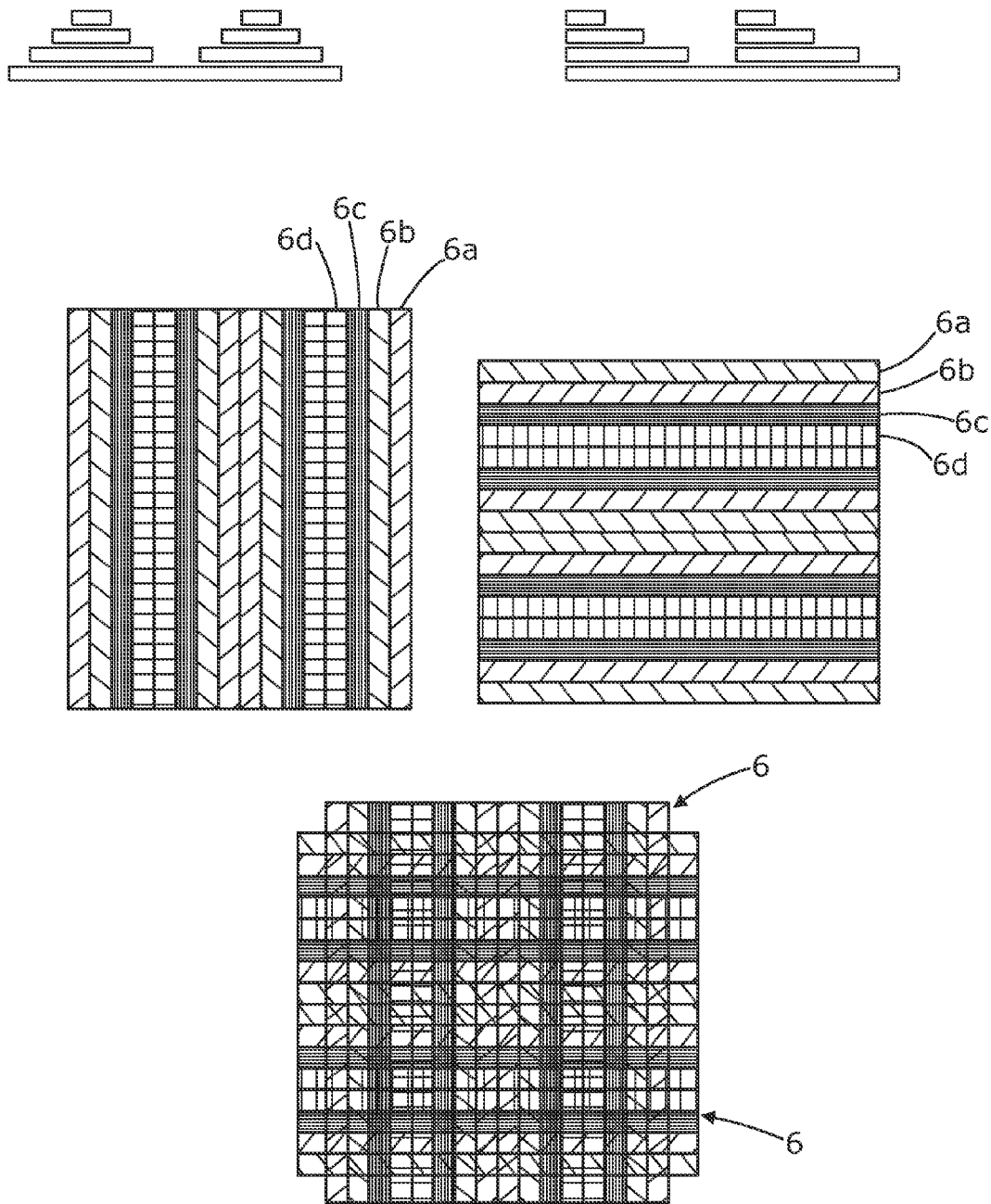

FIGS. 13a and 13b illustrate an alternative construction of interference plate 6. In this example the interference plate 6 is formed of four layers of material 6a to 6d, such as foil. The first layer is not perforated. The second layer 6b includes apertures 6b' of a first width. The third layer 6c includes apertures 6c' of a second width, and the fourth layer 6d includes apertures 6d' of a third width. When stacked with the centres of the apertures 6b' to 6d' aligned the resulting structure has a cross-section 6'. When the layers 6a to 6d are stacked with the edges of the apertures aligned the resulting structure has a cross-section 6".

The structures 6' 6" each provide elongate regions of differing thickness.

In FIG. 13b, two of the resulting interference plates 6 are stacked with the apertures aligned perpendicular to one another. The resulting interference plate provides an array of square regions, wherein adjacent regions are of differing thickness.

Figure 14:
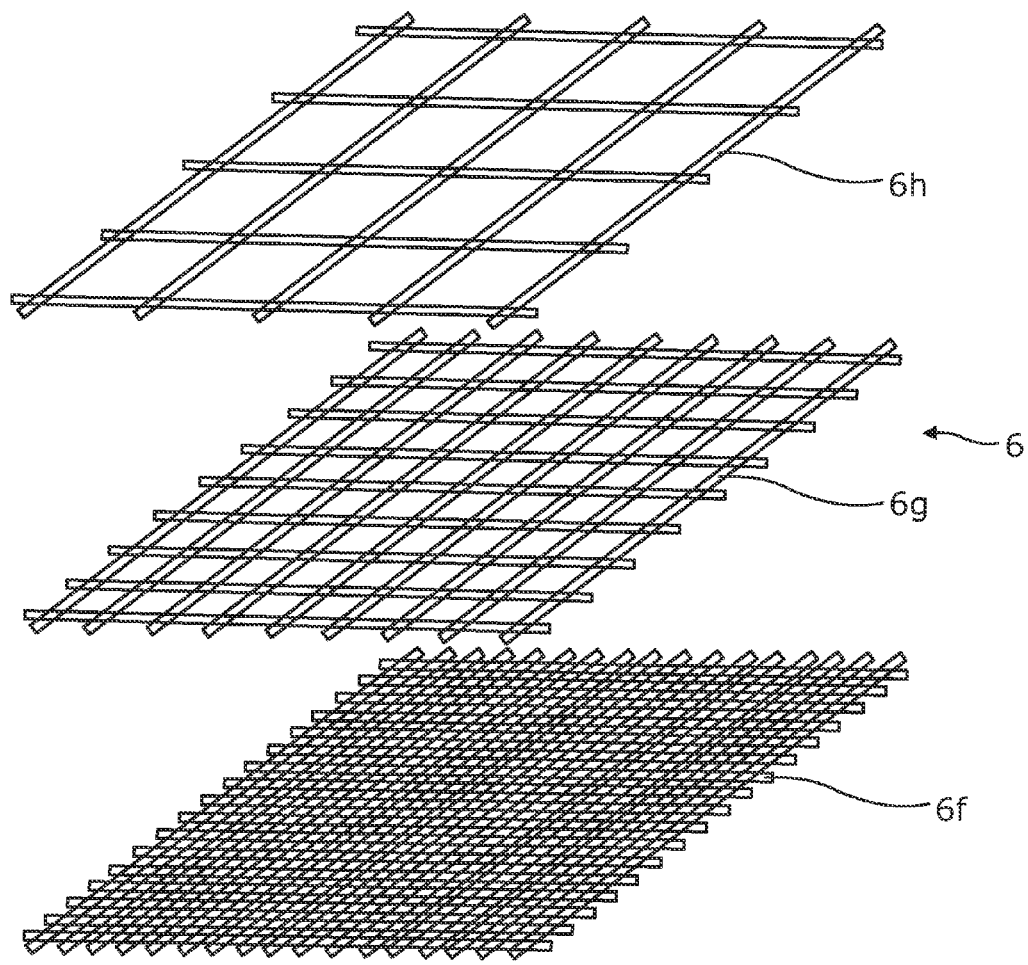
FIG. 14 is an exploded view of an interference plate built up from a number of layers of wire mesh.

FIG. 14 illustrates another alternative arrangement of interference plate 6 comprising three layers 6f to 6h of wire mesh, each of differing mesh size. When stacked one on top of the other, in some regions incident x-rays will impinge upon the wires of the first layer 6f, in other regions incident x-rays will impinge upon wires of the second layer 6g, and in other regions incident x-rays will impinge upon wires of the third layer 6h. Further, in other regions incident x-rays will impinge upon a combination of some of the wires of more than one of the layers 6f, 6g and 6h. Further, there will be regions where no wire is present and hence x-rays incident on these regions will pass through unperturbed.

Figure 15:
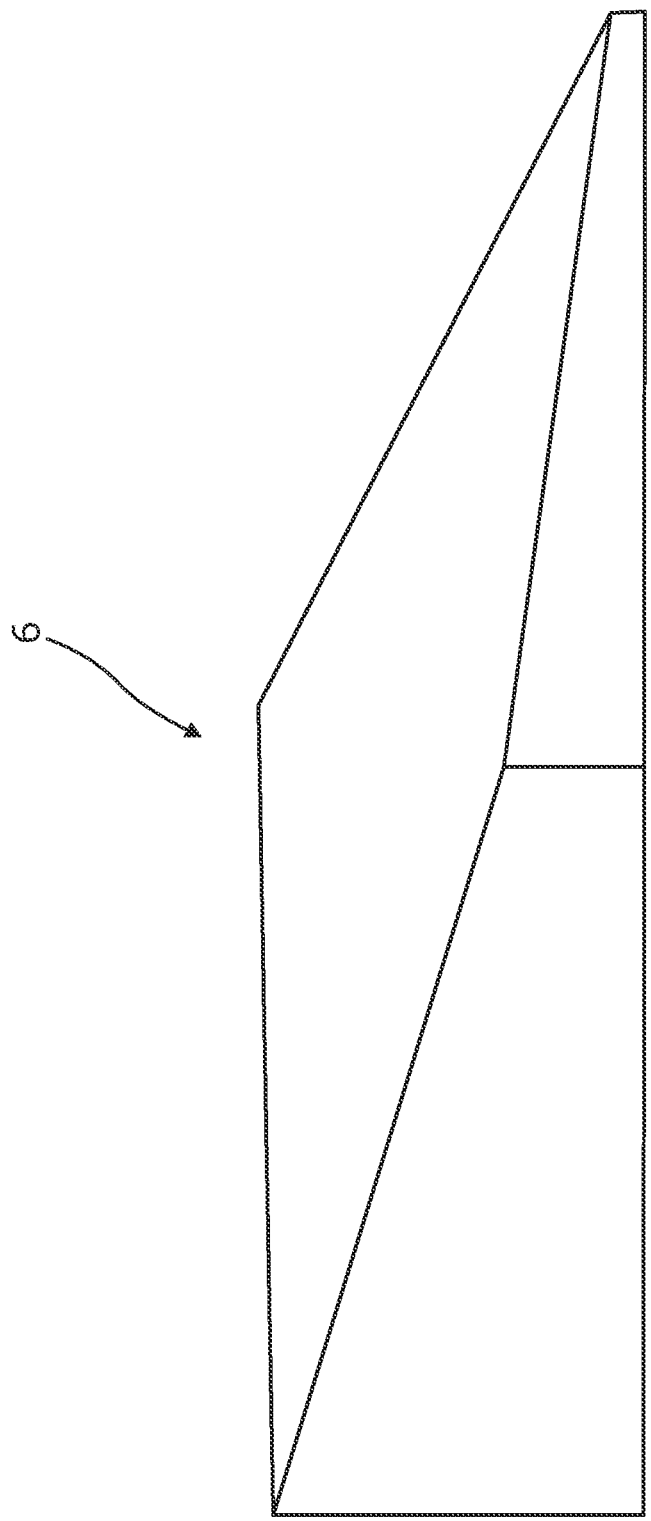
FIG. 15 is a schematic representation of an interference plate having a thickness which varies in two directions of the plate.

In FIG. 15 the interference plate 6 comprises a block of material that is square in plan view and which varies in thickness along two axes across the plate. Hence, the thickness of the material changes continuously across the plate. In this case the actual size of the region is determined by a pixellation grid, for example that of the detector camera. In the case of an interference plate 6 as illustrated in FIG. 15 the difference in the mean thickness of adjacent regions must be sufficient to create a detectable difference in perturbation of an incident x-ray.

Figure 16A:
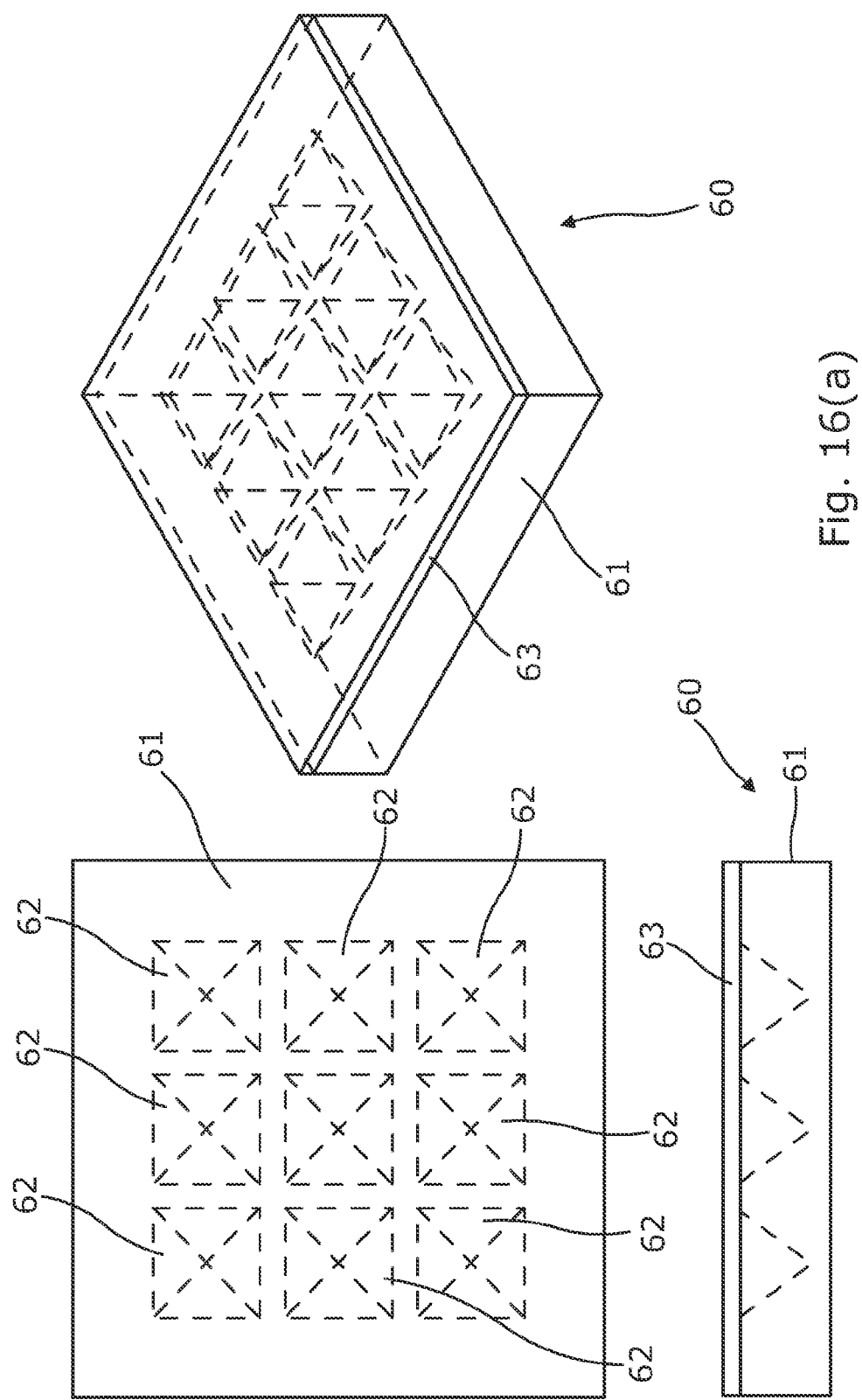
FIG. 16a is schematic, top plan and side views of an alternative embodiment of an interference plate.
Figure 16B:
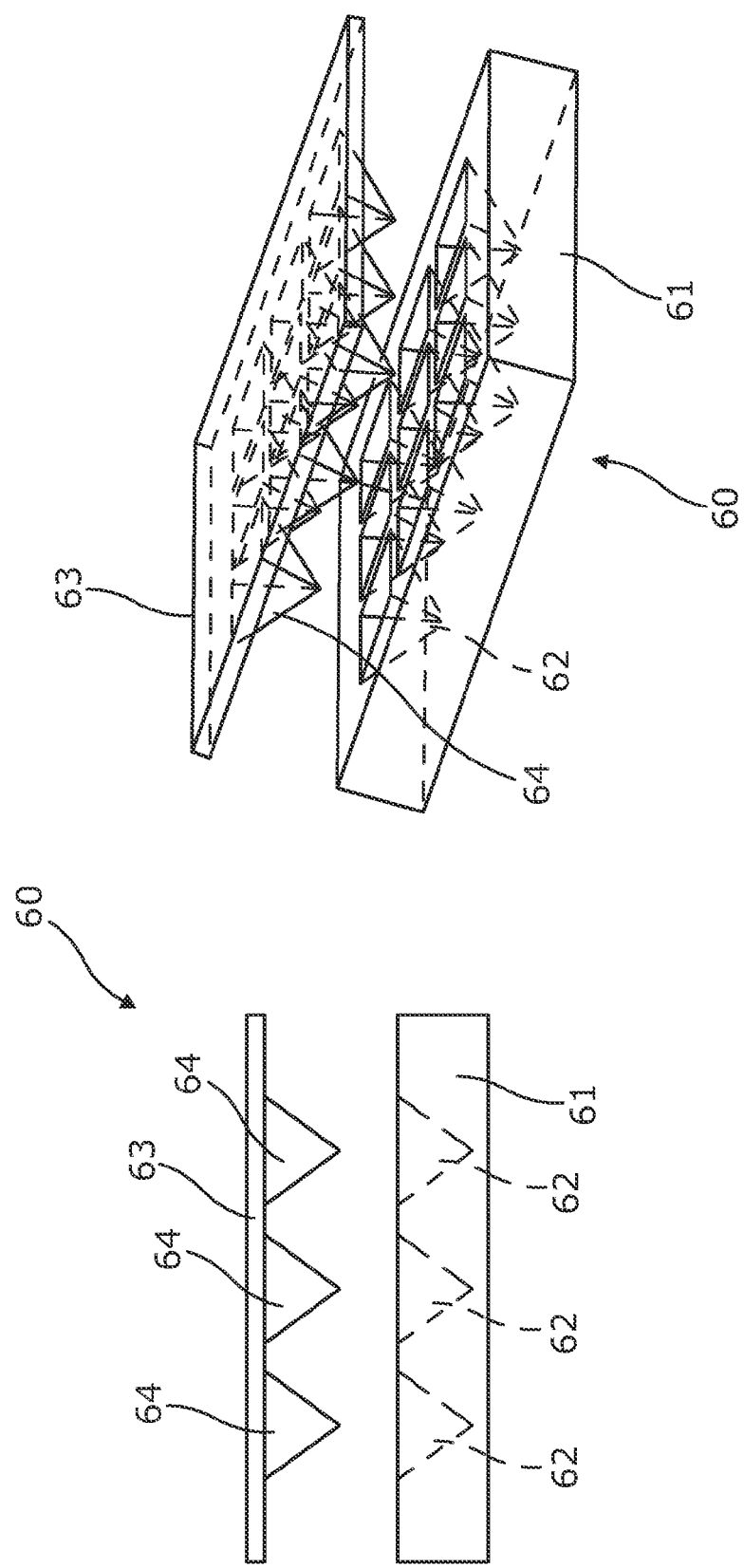

Referring now to FIGS. 16a and 16b, there is shown a further alternative construction of interference plate 60 comprising a first layer 61 and a second layer 63. The first layer 61 is formed of a silicon wafer and having formed therein a multiplicity of depressions 62. In the illustrated example the depressions have a depth of 800 micron. The depressions are formed by etching. It is known that strong alkaline wet etchants such as potassium hydroxide or tetra methyl ammonium hydroxide will preferentially etch certain crystal planes of silicon compared to others due to a difference in the bond strength of silicon atoms in the different crystal planes. The {111} crystal planes are amongst the most resistant to the etchants and so the {100} and {110} planes will be etched at far greater rates than the {111} planes. The silicon wafer from which the first layer 61 is formed is a {100} oriented. A mask defining the array of depressions 62 is applied to a surface of the silicon wafer and an alkaline etchant applied. Where the alkaline etchant is in contact with the silicon it begins to etch down forming square based pyramidal shaped depressions 62. The sloping side-walls of the depressions 62 are the {111} planes of silicon and thus are angled at 54.7 degrees compared to the surface of the {100} silicon wafer. The etching process is allowed to proceed until the {111} side walls converge to form the apex of a pyramid shaped depression 62.

The etchant used to create the depressions 62 was potassium hydroxide. The mask used to form the depressions 62 corresponds in shape to the plan view shown in FIG. 16a. In the illustrated example, the depressions are set out on a 1 mm×1 mm centre to centre grid. The distance between adjacent depressions 62 is approximately 50 microns.

The number of depressions may be increased or decreased by increasing or decreasing the distance between the centres of the depressions. When the distance between depressions is changed the depth of the depression and hence the size of the base of the depression will change, the size of the base being a function of the depth of the depression and the wall angle of 54.7 degrees. For example, the depth of each depression may be reduced to 100 micron.

FIGS. 16a and 16b illustrate a part of an interference plate. The interference plate might measure 26 cm×15 cm for example, and the depressions may be on a grid that is smaller than the 1 mm×1 mm centre to centre grid illustrated here.

The second layer 63 is formed of metal such as nickel, copper or tin. It is this metal second layer 63 which perturbs the x-rays incident upon it, each pyramidal protrusion providing a substantially infinite number of regions of different thickness as the thickness of the metal changes along the slope of the walls of the pyramid. The first layer serves to assist in manufacture of the interference plate and post manufacture to support and protect the metal layer 63. As can be seen from FIGS. 16*a* and 16*b*, the second layer 63 includes pyramidal shaped protrusions 64 and a backing plate 65. The second layer 63 is formed by deposition molten metal on to the surface of the first layer 61, the molten metal filling the pyramidal depressions 62 and forming a thin backing plate 65 (in the order of a few microns) covering the surface of the first layer 61. The metal of the second layer 63 between adjacent pyramidal protrusions may be considered as a region of different thickness to an adjacent region, perturbing the x-ray energy spectrum differently to the metal of the adjacent pyramidal protrusions.

The interference plate 60 may be attached to a scintillator by mechanical clamping or adhesive for example.

Interference plates (which may also be referred to as a multi-absorption plate) may be formed using three-dimensional printing techniques.

Figure 17:
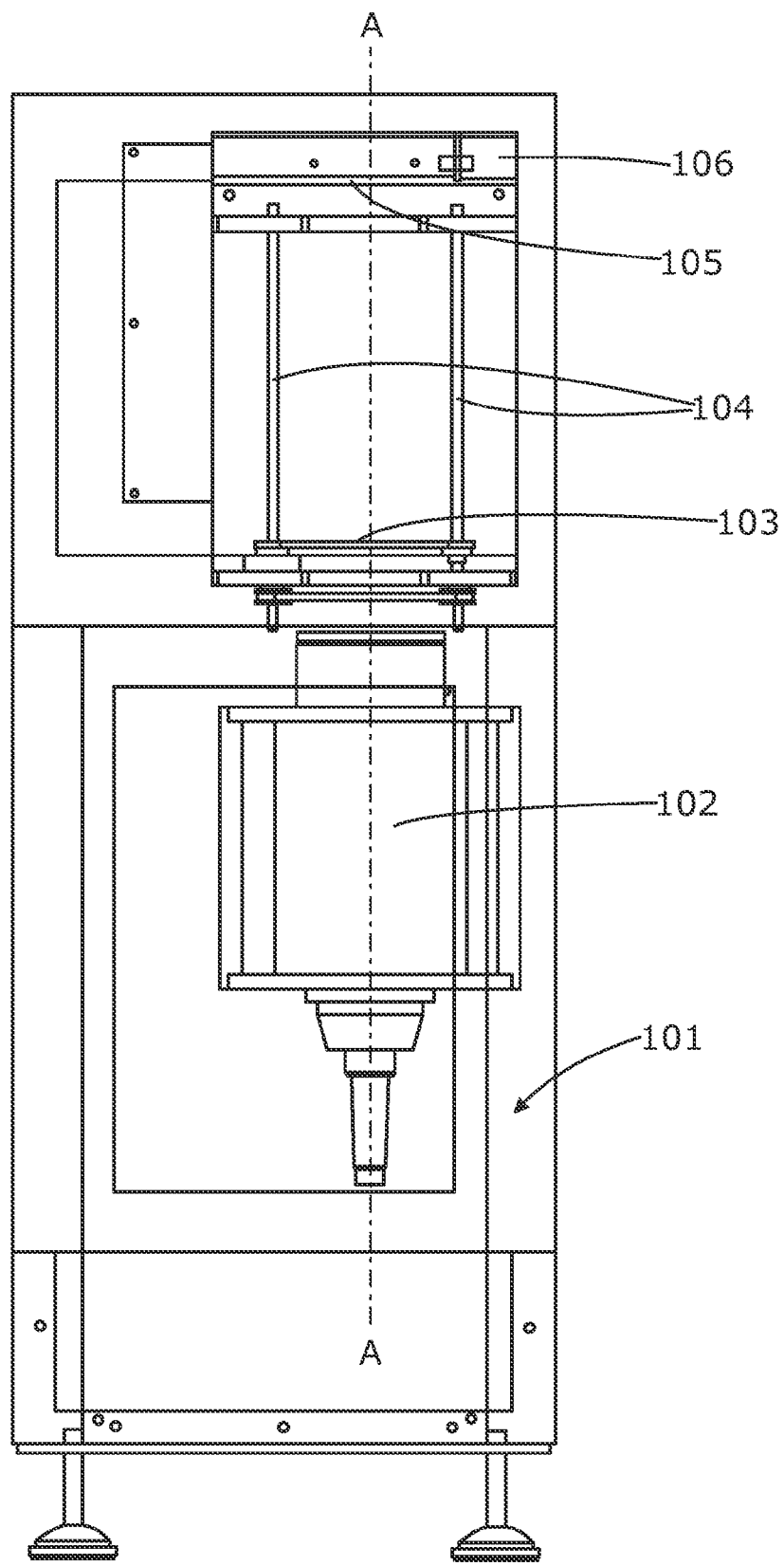
FIG. 17 illustrates an apparatus according to the invention.

Referring now to FIG. 17, there is shown a laboratory scale apparatus 100 according to the invention. The apparatus includes a cabinet 101 in which is mounted an x-ray source 102, a position for a material under test in the form of a sample stage 103 which is mounted on rails 104 so that the position of the stage may be adjusted. The apparatus 100 further includes an interference, or multi-absorption, plate 105 and an x-ray detector 106. The detector 106 forms part of an x-ray camera which includes a scintillator for converting the x-ray wavelength photons of the x-ray shadow image into visible wavelength photons. The camera captures an image which may then be analysed.

To determine a material property of a substance the substance is positioned on the sample stage 103 and the x-ray source 102 is caused to direct an x-ray energy spectrum through the so positioned sample, the plate 105 to impinge upon the detector 106. Visible wavelength photons emitted by the member configured to convert incident x-ray wavelength photons into visible wavelength photons are then analysed according to the following steps:

Step (i)—The detector 106 is pixelated: the intensity of visible wavelength photos recorded by the detector for each pixel is compared with the recorded intensity for its adjacent pixels and the differences in intensity are recorded;

Step (ii)—The intensity of visible wavelength photos recorded by the detector for each pixel is compared with the recorded intensity for its adjacent pixels and the differences in intensity are recorded without a substance present in the apparatus;

Step (iv)—The current differences between recorded intensities between adjacent pixels as determined with by the method steps (i) and (ii) are compared;

Step (v)—Following the method steps (i) to (iv) for at least one known material and storing the differences in a database; and Step (vi)—Comparing the differences between recorded intensities for a substance under test with the differences between recorded intensities for known substances from the database.

The invention claimed is:

1. X-ray imaging and materials identification apparatus, the apparatus including an x-ray detector comprising:
    a single member configured to convert incident x-ray wavelength photons into emitted visible wavelength photons,
    a position for a material under test,
    an x-ray source, and
    a structure configured to perturb an x-ray energy spectrum, wherein the single member, the position for a material under test, the x-ray source, and the structure configured to perturb an x-ray energy spectrum each lie on a common axis, wherein:
    the x-ray source is arranged to direct an x-ray energy spectrum along the common axis to impinge upon the member, the structure configured to perturb the x-ray energy spectrum, and the position for material under test,
    said structure lies between the x-ray source and the single member to one side of the position for material under test intersecting the common axis,
    the structure configured to perturb an x-ray energy spectrum comprises at least three adjacent regions, each different from each other and having a different x-ray energy spectrum perturbing characteristic, and
    a difference between adjacent regions of the structure configured to perturb the x-ray energy spectrum includes the thickness of the material of the structure in adjacent regions.

2. X-ray imaging apparatus according to claim 1, wherein the member configured to convert incident x-ray wavelength photons into emitted visible wavelength photons is a scintillator.

3. X-ray imaging apparatus according to claim 2, wherein the scintillator includes a scintillator layer and a backing layer.

4. An x-ray imaging apparatus according to claim 1, wherein the at least three regions are formed in an array.

5. An x-ray imaging apparatus according to claim 4, wherein the array comprises an x by y array wherein the multiple of x and y is not fewer than three.

6. An x-ray imaging apparatus according to claim 4, wherein the array repeats itself in the structure.

7. An x-ray imaging apparatus according to claim 4, wherein the structure includes a multiplicity of arrays.

8. An x-ray imaging apparatus according to claim 1, wherein the structure is one of: planar and non-planar.

9. An x-ray imaging apparatus according to claim 8, wherein the structure is curved in at least one plane.

10. An x-ray imaging apparatus according to claim 1, wherein the difference between adjacent regions of the structure configured to perturb the x-ray energy spectrum also includes a material from which the individual adjacent regions of the structure are formed.

11. An x-ray imaging apparatus according to claim 10, wherein the individual regions of the structure include discrete layers.

12. An x-ray imaging apparatus according to claim 11, wherein the discrete layers differ and the difference between discrete layers is selected from the group comprising: the discrete layers differ in their thicknesses between regions; the discrete layers differ in their thicknesses within a region; the discrete layers differ in the materials from which they are formed between regions; the discrete layers differ in the materials from which they are formed within a region; the discrete layers differ in their numbers between regions; and the discrete layers differ in their numbers within a region.

13. An x-ray imaging apparatus according to claim 10, wherein the structure includes a plurality of discrete layers and at least one of the discrete layers includes at least one aperture.

14. An x-ray imaging apparatus according to claim 13, wherein the discrete layers each include at least one aperture and wherein apertures of different layers within the structure are of different dimensions.

15. An x-ray imaging apparatus according to claim 12, wherein the discrete layers are formed of one of: foil and mesh.

16. An x-ray imaging apparatus according to claim 10, wherein the structure changes in thickness continuously across the structure in at least one direction.

17. An x-ray imaging apparatus according to claim 16, wherein the structure changes in thickness continuously across the structure in two orthogonal directions.

18. An x-ray imaging apparatus according to claim 10, wherein the structure includes one of: a plurality of protrusions and a plurality of depressions, a thickness of said protrusions and depressions changing in at least one direction thereof, each protrusion and depression providing the at least three adjacent regions configured to perturb the x-ray energy spectrum.

19. An x-ray imaging apparatus according to claim 18, wherein the protrusions and depressions are pyramidal in shape.

20. An x-ray imaging apparatus according to claim 19, wherein the structure comprises a non-metallic layer having a multiplicity of depressions formed therein, each depression filled with metal.

21. An x-ray imaging apparatus according to claim 20, wherein the structure comprises a first non-metallic layer having a multiplicity of depressions formed therein and a second metallic layer including a corresponding number of protrusions each protrusion mating with a corresponding depression.

22. An x-ray imaging apparatus according to claim 21, wherein the second layer covers the surface of the first layer in which the openings to the depressions are situated.

23. An x-ray imaging apparatus according to claim 19, wherein adjacent depressions and protrusions are separated from one another by x-ray perturbing material and wherein the material separating adjacent depressions and protrusions constitute one of the at least three adjacent regions.

24. An x-ray imaging apparatus according to claim 20, wherein the non-metallic layer is formed of silicon.

25. An x-ray imaging apparatus according to claim 20, wherein the structure comprises a substrate and the said plurality of regions are one of: formed in the substrate; formed on the substrate; and formed in and on the substrate.

26. An x-ray imaging apparatus according to claim 2, wherein the scintillator is formed of a scintillator material having one of a flat energy dependence and a non-flat energy dependence.

27. An x-ray detector suitable for use in an x-ray imaging and materials identification apparatus according to claim 1, wherein the x-ray detector comprises a single member configured to convert incident x-ray wavelength photons into emitted visible wavelength photons and a separate structure for alignment with an x-ray energy spectrum source, the structure configured to perturb the x-ray energy spectrum, and the structure comprising at least three regions, each different from each other and having a different x-ray energy spectrum perturbing characteristic.

* * * * *